(12) United States Patent
Sherley et al.

(10) Patent No.: US 7,824,912 B2
(45) Date of Patent: *Nov. 2, 2010

(54) METHODS FOR EX VIVO PROPAGATION OF ADULT HEPATIC STEM CELLS

(75) Inventors: James L. Sherley, Boston, MA (US); Krisha Panchalingam, Medford, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 125 days.

This patent is subject to a terminal disclaimer.

(21) Appl. No.: 11/472,238

(22) Filed: Jun. 21, 2006

(65) Prior Publication Data

US 2007/0020610 A1    Jan. 25, 2007

Related U.S. Application Data

(60) Provisional application No. 60/693,493, filed on Jun. 23, 2005.

(51) Int. Cl.
*C12N 15/85* (2006.01)
*A01K 67/00* (2006.01)

(52) U.S. Cl. .................. 435/326; 435/1.1; 435/325; 435/347; 435/370; 435/377; 435/384

(58) Field of Classification Search .................. None
See application file for complete search history.

(56) References Cited

U.S. PATENT DOCUMENTS

| | | | |
|---|---|---|---|
| 5,474,931 A | 12/1995 | DiSorbo et al. | |
| 5,741,646 A | 4/1998 | Sherley et al. | |
| 5,801,159 A | 9/1998 | Miller et al. | |
| 6,146,889 A | 11/2000 | Reid et al. | |
| 6,242,252 B1 | 6/2001 | Reid et al. | |
| 2003/0133918 A1* | 7/2003 | Sherley | .......... 424/93.21 |
| 2004/0018620 A1 | 1/2004 | Sherley | |
| 2005/0074874 A1 | 4/2005 | Sherley | |
| 2005/0272147 A1 | 12/2005 | Sherley | |

FOREIGN PATENT DOCUMENTS

| | | |
|---|---|---|
| WO | WO 97/24458 A1 | 7/1997 |
| WO | WO 02/08451 A2 | 1/2002 |
| WO | WO 02/062969 A2 | 8/2002 |
| WO | WO 02/090992 A2 | 11/2002 |
| WO | WO 03/006613 A2 | 1/2003 |
| WO | WO 03/069972 A2 | 8/2003 |

OTHER PUBLICATIONS

Lee et al Biotechnol. Bioeng. 83:760-771; 2003.*
ATCC; Cell Lines and Hybridomas; 8th ed.; p. 518 (1994).
Bartel, T. et al.; Biochimica et Biophysica Acta.; 1035:331-339 (1990).
Brenner, M. K.; Gene Transfer to Hematopoietic Cells; New Engl. J. Med.; 335(5):337-339 (1996).
Cairns, J.; Mutation Selection and the Natural History of Cancer; Nature; 255:197-200 (May 15, 1975).
Fuchs, E. and Segre, J. A.; Stem Cells: A New Lease on Life; Cell; 100:143-155 (Jan. 7, 2000).
Ganassin, R.C. et al.; Journal of Cellular Physiology; 160:409-416 (1994).
Gridelli, B. and Remuzzi, G.; Strategies for Making More Organs Available for Transplantation; New Engl. J. Med.; 343(6):404-410 (Aug. 10, 2000).
Hayashi, Y. et al.; Experimental Cell Research; 185:217-228 (1989).
Hirai, S. et al., Biochemical Pharmacology; 45(8):1695-1701 (1993).
Lee, Hsuan-Shu et al.; Clonal Expansion of Adult Rat Hepatic Stem Cell Lines by Suppression of Asymmetric Cell Kinetics (SACK); Biotechnology and Bioengineering; 83(7):760-771 (Sep. 30, 2003).
Liu, Y., Bohn, S.A., and Sherley, J.L.; Inosine-5'-Monophosphate Dehydrogenase is a Rate-Determining Factor for p53-Dependent Growth Regulation; Molecular Biology of the Cell; 9:15-28 (1998).
Liu, Y., Riley, L.B., Bohn, S.A., Boice, J.A., Stadler, P.B., and Sherley, J.L.; Comparison of Bax, Waf1, and IMP Dehydrogenase Regulation in Response to Wild-Type p53 Expression Under Normal Growth Conditions; Journal of Cellular Physiology; 177:364-376 (1998).
Loeffler, M. and Potten, C.S.; Stem Cells and Cellular Pedigrees—A Conceptual Introduction; Stem Cells; (San Diego, CA: Harcourt Brace & Co.), pp. 1-27 (1997).
Merok, J.R. and Sherley, J.L.; Breaching the Kinetic Barrier to In Vitro Somatic Stem Cell Propagation; Journal of Biomedicine Biotechnology; 1(1):25-27 (2001).

(Continued)

*Primary Examiner*—J D Schultz
(74) *Attorney, Agent, or Firm*—Nixon Peabody LLP

(57) ABSTRACT

The present invention is directed to methods for readily propagating somatic liver stem cells. The methods comprise enhancing guanine nucleotide (GNP) biosynthesis, thereby expanding guanine nucleotide pools. This in turn conditionally suppresses asymmetric cell kinetics in the explanted cells. The methods of the invention include pharmacological methods and genetic methods. For example, the resulting cultured somatic liver stem cells can be used for a variety of applications including cell replacement therapies, gene therapies, drug discovery applications, and tissue engineering applications, such as the generation of artificial liver.

11 Claims, 17 Drawing Sheets

OTHER PUBLICATIONS

Moore, K.A. et al..; In Vitro Maintenance of Highly Purified, Transplantable Hematopoietic Stem Cells; Blood; 89(12):4337-4347 (Jun. 15, 1997).

Phillips, R.L., Ernst, R.E., Brunk, B., Ivanova, N., Mahan, M.A., Deanehan, J.K., Moore, K.A., Overton, G.C., and Lemischka, I.R.; The Genetic Program of Hematopoietic Stem Cells; Science; 288:1635-1640 (Jun. 2, 2000).

Podolsky, D.K.; Regulation of Intestinal Epithelial Proliferation: a Few Answers, Many Questions; American Journal of Physiology; 264:G179-G186 (1993).

Potten, C.S. and Grant, H.K.; The Relationship Between Ionizing Radiation-Induced Apoptosis and Stem Cells in the Small and Large Intestine; British Journal of Cancer; 78(8):993-1003 (1998).

Potten, C.S. and Morris, R.J.; Epithelial Stem Cells In Vivo; J. Cell Sci. Suppl.; 10:45-62 (1988).

Rambhatla, L., Bohn, S.A., Stadler, P.B., Boyd, J.T., Coss, R.A., and Sherley, J.L.; Cellular Senescence: ex vivo p53-Dependent Asymmetric Cell Kinetics; Journal of Biomedicine Biotechnology; 1(1):28-37 (2001).

Reisner, Y., Itzicovitch, L., Meshorere, A., and Sharon, N.; Hemopoietic Stem Cell Transplantation Using Mouse Bone Marrow and Spleen Cells Fractionated by Lectins; Proc. Natl. Acad. Sci. USA; 75(6):2933-2936 (Jun. 1978).

Sherley, J.L.; Guanine Nucleotide Biosynthesis is Regulated by the Cellular p53 Concentration; Journal of Biological Chemistry; 266(36):24815-24828 (1991).

Sherley, J.L., Stadler, P.B. and Stadler, J.S.; A Quantitative Method for the Analysis of Mammalian Cell Proliferation in Culture in Terms of Dividing and Non-dividing cells; Cell Proliferation; 28:137-144 (1995).

Sherley, J.L., Stadler, P.B. and Johnson, D.R.; Expression of the Wildtype p53 Antioncogene Induces Guanine Nucleotide-Dependent Stem Cell Division Kinetics; Proc. Natl. Acad. Sci. USA; 92:136-140 (Jan. 1995).

Sherley, J.L.; IMPDH: A Regulator of Somatic Stem Cell Kinetics; Abstracts of Papers American Chemical Society; 220(1):CARB 10 (2000).

Sherley, J.L. (published on-line); Adult Stem Cell Differentiation: What Does it Mean?

Talbot, N.C. et al.; Cloning and Stem Cells; 6(1):37-47 (Nov. 1, 2004).

Wagers, A.J. et al.; Cell; 116:639-648 (Mar. 5, 2004).

"Notification of Transmittal of the International Search Report and the Written Opinion of the International Searching Authority, or the Declaration" of International Application No. PCT/US2006/024190, with an International Filing Date of Jun. 21, 2006.

Tunstead, J.R. et al., SDB Meeting Abstracts, p. 227, No. 262 (2001). "Molecular Determinants of Asymmetric Stem Cell Kinetics."

Weissman, I.L.; Stem Cells: Units of Development, Units of Regeneration, and Units in Evolution; Cell; 100(1):157-168 (Jan. 7, 2000).

Wilson, J.M.; Vehicles for Gene Therapy; Nature; 365:691-692 (Oct. 21, 1993).

Zimmermann, S. et al.; Leukemia; 17:1146-1149 (2003).

Morris, R. J. et al.; Nature Biotechnology; 22(4):411-417 (2004.

* cited by examiner

SSC ASYMMETRIC KINETICS IN VIVO

A CELL CULTURE MODEL FOR SSC KINETICS

| LIVER # | AGE (YEARS) | GENDER | CELL STRAIN | TOTAL DOUBLINGS | DOUBLING/DAY | SENESCED AT |
|---|---|---|---|---|---|---|
| 1 | 6 | M | CONTROL-a | 24 | 0.12 | PASSAGE 15 |
| | | | CONTROL-b | 10 | 0.05 | PASSAGE 6 |
| | | | Xn | 38 | 0.18 | PASSAGE 24 |
| | | | Hx | 27 | 0.13 | PASSAGE 17 |
| | | | Xs | 34 | 0.15 | PASSAGE 21 |
| 2 | 14 | F | CONTROL | 10 | 0.09 | PASSAGE 5 |
| | | | Hx | 26 | 0.12 | PASSAGE 16 |
| 3 | 1 | M | CONTROL | 24 | 0.21 | n/a |
| | | | Xn | 10 | 0.11 | n/a |
| | | | Hx - a | 30 | 0.29 | n/a |
| | | | Hx - b | 20 | 0.19 | n/a |
| | | | Xs - a | 48 | 0.41 | n/a |
| | | | Xs - b | 21 | 0.18 | n/a |
| 4 | 24 | M | CONTROL | 16 | 0.17 | n/a |
| | | | Xs - a | 26 | 0.31 | n/a |
| | | | Xs - b | 16 | 0.23 | n/a | n/a - NOT SENESCED YET
a, b - REPRESENTS REPLICATE CULTURES WITH MODIFICATIONS

*FIG. 5*

NON-SACK CELL STRAIN

SACK DERIVED CELL STRAIN - TABLE 1: LIVER₃ Xs-a

SACK DERIVED CLONAL CELL STRAIN

METHODS FOR EX VIVO PROPAGATION OF ADULT HEPATIC STEM CELLS

CROSS-REFERENCE TO RELATED APPLICATIONS

This application claims the benefit under 35 U.S.C. §119(e) of U.S. Provisional Patent Application No. 60/693,493 filed Jun. 23, 2005.

GOVERNMENT FUNDING

This invention was supported by the National Institute of Health grant 5-RO1-ES011017-02 and the government of the United States has certain rights thereto.

FIELD OF THE INVENTION

The present application is directed to the ex vivo expansion of post-natal liver stem cells and to their use in cell replacement therapies, gene delivery strategies, drug discovery (e.g. toxicology applications and metabolic profiling) and tissue engineering applications. Preferably somatic liver stem cells from human tissue are used.

BACKGROUND OF THE INVENTION

Stem cells have the ability to differentiate into a variety of cells and tissues. Thus, considerable attention has focused on stem cells and their uses in a multitude of applications, including tissue engineering, tissue regeneration, and gene delivery. Stem cells have been isolated from both embryonic and adult tissues. Somatic stem cells that are derived from adult tissue still have the ability to renew adult tissues (Fuchs and Segre, 2000). Thus, in light of the ongoing controversies surrounding the use of embryonic stem cells, the use of somatic stem cells are a particularly attractive alternative.

The presence of stem cells in somatic tissues has been well established using functional tissue cell transplantation assays (Reisner et al., 1978). However, isolation and propagation of somatic stem cells has proven difficult. Methods to isolate and expand stem cells from somatic tissue, particularly without significant differentiation, are highly desirable. There have been some questions raised regarding how multi-potent adult stem cells are related to embryonic stem cells. Thus, it is important to be able to obtain and cultivate many different types of somatic stem cells. In particular, the availability of a method to propagate liver stem cells from adult tissues would greatly contribute to the treatment of chronic and acute liver failure, the identification of liver stem cell markers, as well as tissue engineering, e.g. generation of artificial liver.

There has been considerable difficulty encountered in obtaining human somatic liver stem cells that can be propagated and cultured ex vivo. One factor is the predominant way somatic stem cells divide is by asymmetric cell kinetics. During asymmetric kinetics, one daughter cell divides with the same kinetics as its stem cell parent, while the second daughter gives rise to a differentiating non-dividing cell lineage. The second daughter may differentiate immediately; or, depending on the tissue, it may undergo a finite number of successive symmetric divisions to give rise to a larger pool of differentiating cells.

Such asymmetric cell kinetics are a major obstacle to somatic cell expansion in vitro (Merok and Sherley, 2001; Rambhatla et al., 2001; Sherley, 2002). In culture, continued asymmetric cell kinetics results in dilution and loss of an initial relatively fixed number of stem cells by the accumulation of much greater numbers of their terminally differentiating progeny. If a sample includes both exponentially growing cells as well as somatic stem cells, the growth of the exponentially growing cells will rapidly overwhelm the somatic stem cells, leading to their dilution. Even in instances where it is possible to select for relatively purer populations, for example by cell sorting, asymmetric cell kinetics prevent expansion.

Furthermore, previous investigative methods for expanding post-natal human liver cells have required the use of feeder layers and biological matrices to maintain the cells in culture. With such methods, post-natal human liver cells could only be maintained for a few passages.

Thus, despite the need for methods to isolate liver stem cells from an individual and expand them ex vivo, it has not been possible to do so.

SUMMARY OF THE INVENTION

We have now invented methods for readily propagating somatic liver stem cells, preferably multi-potent liver stem cells. The methods shift liver stem cells from asymmetric cell kinetics to symmetric cell kinetics, which promote exponential expansion of adult stem cells in culture. The methods do not require a feeder layer or a biological matrix to maintain the cells in culture. Symmetric stem cell kinetics are characterized by divisions that produce two stem cells and no differentiating cells. This shift in kinetics symmetry is referred to as suppression of asymmetric cell kinetics (SACK). The methods comprise enhancing guanine nucleotide (GNP) biosynthesis, thereby expanding guanine nucleotide pools. This in turn conditionally suppresses the asymmetric cell kinetics exhibited by, for example, somatic liver cells. The methods of the invention include pharmacological methods and genetic methods. One preferred method of enhancing guanine nucleotide biosynthesis is to bypass or override normal inosine-5'-monophosphate dehydrogenase (IMPDH) regulation. IMPDH catalyzes the conversion of inosine-5' monophosphate (IMP) to xanthosine monophosphate (XMP) for guanine nucleotide biosynthesis. This step can be bypassed or overridden by providing a guanine nucleotide precursor (GNPr) such as xanthosine or hypoxanthine, respectively. The next metabolite in the GNP pathway is guanine monophosphate (GMP), which in turn is metabolized to the cellular guanine nucleotides. The resulting cultured somatic liver stem cells can be used for a variety of applications including cell replacement therapies, identification of liver stem cell markers, gene therapies, and tissue engineering.

In one preferred embodiment of the invention, somatic liver stem cells are removed and cultivated in the presence of compounds such as guanine nucleotide precursors (GNPrs), which lead to increased guanine nucleotide pools. Preferably, the GNPr is xanthosine or hypoxanthine. Even more preferably, the GNPr is xanthine.

In another preferred embodiment of the invention, the somatic liver stem cells are propagated in a primitive undifferentiated state but retain the ability to be induced to produce differentiating progeny cells. Differentiation can be induced by the site where the cell is placed in a subject or appropriately engineered material.

Another preferred embodiment provides for deriving clonal lines of somatic liver stem cells by limiting dilution plating or single cell sorting in the presence of compounds which enhance guanine nucleotide biosynthesis, thereby suppressing asymmetric cell kinetics.

In another embodiment of the invention, genes that lead to constitutive upregulation of guanine nucleotides (GNPs), including upregulation of guanine ribonucleotides (rGNPs), are introduced into the somatic liver stem cells. Preferred genes are those that encode inosine-5' monophosphate dehydrogenase (IMPDH) or xanthine phosphoribosyltransferase (XPRT). More preferably, XPRT.

Another embodiment of the invention provides methods for administering liver stem cells to a patient in need thereof, comprising the steps of (1) isolating the stem cells from an individual; (2) expanding for example the somatic liver stem cells in culture using pharmacological or genetic methods to enhance guanine nucleotide biosynthesis to expand guanine nucleotide pools and suppress asymmetric cell kinetics; and thereafter, (3) administering the expanded liver stem cells to said individual in need thereof.

Further embodiments of the invention provide for additional manipulations, including genetic manipulation of the somatic liver stem cells prior to administration to the individual.

Another preferred embodiment provides for the use of expanded somatic liver stem cells to identify unique liver stem cell markers and molecular probes specific for such stem cells in tissues or tissue cell preparations.

BRIEF DESCRIPTION OF THE DRAWINGS

FIG. 1A, In vivo, somatic stem cells (SSC, bold-lined circles) can exhibit one of three division programs: 1) Highly restricted symmetric kinetics that produce two similar somatic stem cells (brackets); 2) Dormancy (stippled circle); and 3) Asymmetric kinetics, the most populated somatic stem cell kinetics state in most tissues. Asymmetric somatic stem cells underlie turnover units (TU; Hererro-Jimenez et al., 1998). Turnover units are comprised of three cell types: an asymmetric somatic stem cell, transit cells (thin-lined open circle), and mature, differentiated, non-dividing terminal cells (closed circle). Asymmetric somatic stem cells divide to produce another asymmetric somatic stem cell and a transit cell. Depending on the type of tissue, the transit cell may undergo no further division, or a finite number of successive divisions may occur. However, all transit lineage cells mature into differentiated, non-dividing terminal cells. FIG. 1B, Model cells with conditional asymmetric cell kinetics (due to p53-induced down-regulation of IMPDH) can be induced to switch from symmetric kinetics (left compartment) to two types of asymmetric kinetics programs (right compartment) that have the key features of asymmetric somatic stem cell kinetics in vivo.

FIG. 5 shows a chart of liver cell strains that have been established using the suppression of asymmetric cell kinetics (SACK) method. Non-SACK conditions (Control) and 3 different SACK agents (HX, Xs & Xn) were used in expanding post-natal liver stem cells. HX=hypoxanthine; Xs=xanthosine; Xn=xanthine.

In FIGS. 9A and 9B, the left major peak corresponds to G1 cells with 2N DNA content. The right major peak corresponds to G2/M cells with 4N DNA content. S phase cells with variable DNA content contribute the fluorescence area between the major two peaks. The G1 peak that remains in FIG. 9D after colcemid arrest reflects the large fraction of arrested cells produced by asymmetric self-renewal in cultures of p53-expressing cells. The colcemid arrest profile of symmetrically cycling p53-null cells (FIG. 9C) is consistent with their known very low fraction of non-cycling cells.

FIG. 10A, SACK Culture-No Colcemid; FIG. 10B Clonal SACK culture C1-No Colcemid; FIG. 10C, SACK culture-Colcemid; FIG. 10D, Clonal SACK culture C1-Colcemid; FIG. 10E, Non-SACK Culture-No Colcemid; FIG. 10F Non-SACK culture-Colcemid. In the polyclonal SACK culture, 28% of the cells were non-cycling, compared to 96% of the non-SACK strain cells. These data indicate that both SACK and non-SACK cultures produce non-cycling cells. However, under these conditions, there is very limited proliferative capacity in the non-SACK cultures, consistent with their earlier senescence. In the clonal sub-strain C1, 55% of the cells were non-cycling.

FIGS. 11A and 11C, α-fetoprotein; FIGS. 11B and 11D albumin secretion. In human serum cultures, a species consistent with the modified proalbumin (MW ranges from 80-84 kDA) was observed until 48 hrs; and at 72 hrs appeared to be converted to albumin (FIG. 11B). FIG. 11C and FIG. 11D show α-fetoprotein and albumin secretion in subcloned C1 cells respectively.

FIG. 14A, cells were grown in a collagen-Matrigel™ sandwich with serum supplemented medium. FIG. 14B, cells were grown under routine culture conditions, but with serum-free medium. Data are the mean of replicate assays (n=2). Error bars indicate the standard deviation of replicate assays.

DETAILED DESCRIPTION OF THE INVENTION

Figure 1A:
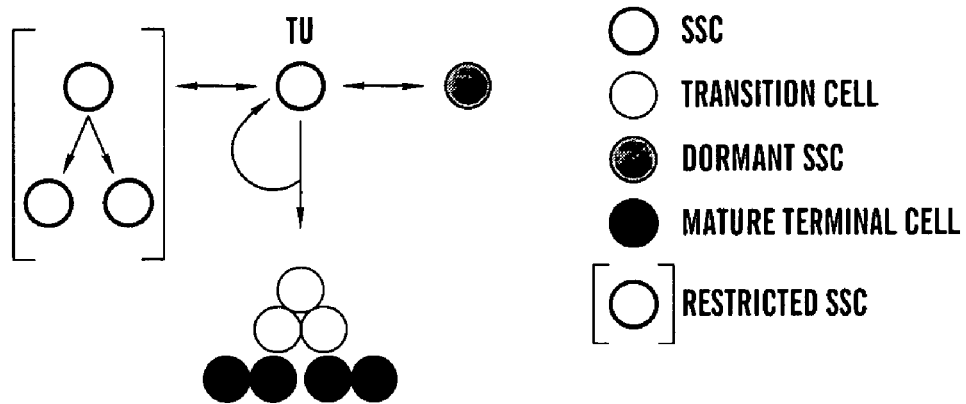
FIGS. 1A-1B depict the in vivo asymmetric kinetics of somatic stem cells.

We have now discovered methods for propagating somatic liver stem cells by conditionally suppressing asymmetric cell kinetics in cultured cells. This is accomplished by enhancing guanine nucleotide biosynthesis, thereby expanding guanine nucleotide pools, including expanding guanine ribonucleotide pools. The methods of the invention include pharmacological methods and genetic methods. Somatic liver stem cells can be used for a variety of applications including, but not limited to, cell replacement therapies in order to treat for example, drug screening assays (e.g. toxicology assays), chronic and acute liver failure, gene delivery, and tissue engineering.

In one embodiment, a method of culturing and expanding somatic liver stem cells in vitro is provided. The method comprises a) isolating somatic liver stem cells from a mammal; and b) culturing said somatic liver stem cells in a culture medium that permits cell growth under conditions, and for a time sufficient, to permit cell growth, wherein a guanine nucleotide biosynthesis pathway in said somatic liver stem cells is enhanced by an agent present in the culture medium, or by a genetic manipulation to said somatic liver stem cells, resulting in conversion of the stem cells from asymmetric cell kinetics to symmetric cell kinetics resulting in enhanced proliferation of said liver stem cells with a reversibly reduced production of differentiating progeny cells.

In one embodiment the agent is present in said media and the agent is a guanine nucleotide precursor, an analogue or derivative thereof. In one embodiment, the guanine nucleotide precursor is xanthosine or hypoxanthine. In one embodiment the guanine nucleotide precursor is xanthine.

In one embodiment the guanine nucleotide precursor is present in an amount of 10-5000 μM. In one embodiment the guanine nucleotide precursor is present in an amount of at least 50 μM, for example, 50-1500 μM. Any amount within that range can be used. For example, 60, 65, 83, 95, 125, 275, 500, . . . 1500 μM.

In one embodiment, genetic manipulation of the somatic liver stem cells is used, resulting in conversion of the stem cells from asymmetric cell kinetics to symmetric cell kinetics resulting in enhanced proliferation of said liver stem cells with a reversibly reduced production of differentiating progeny cells.

In one embodiment, the genetic manipulation results in upregulation of guanine nucleotide biosynthesis.

In one embodiment, the genetic manipulation comprises expressing a gene encoding inosine-5' monophosphate dehydrogenase (IMPDH) or xanthine phosphoribosyltransferase (XPRT) in the cultured somatic liver stem cells.

In one embodiment, the gene encodes xanthine phosphoribosyltransferase.

In one embodiment, cells are cultured at a high cell density.

A method for administering somatic liver stem cells to a subject is also provided. The method comprises (a) isolating somatic liver stem cells from said individual or a matched individual; (b) culturing said isolated somatic liver stem cells in a medium that will promote growth of said cells and under conditions sufficient for such growth; (c) adding a substituent to said medium to enhance guanine nucleotide biosynthesis suppressing asymmetric kinetics; (d) culturing said isolated somatic liver stem cells for at least 10 days after said substituent is added to expand said isolated somatic cells; and, (e) administering said isolated liver stem cells of step (d) to said individual.

A method for deriving clonal cells lines of somatic liver stem cells by isolating somatic liver stem cells from a mammal is also provided. The method comprises performing limiting dilution plating or cell sorting of said somatic liver stem cells to isolate single somatic liver stem cells, and culturing and expanding said single somatic stem cells using the method of culturing and expanding somatic liver stem cells in vitro described above.

In one embodiment, the method for deriving clonal cell lines of somatic liver stem cells comprises culturing to confluence a starting liver cell population containing a population of somatic liver stem cells, and culturing and expanding said somatic liver stem cells using the method of culturing and expanding somatic liver stem cells in vitro described above. In one embodiment, the starting liver cell population containing somatic liver stem cells is cultured to confluence in media supplemented with TGF-β and EGF. In one embodiment, the media contains about 1% serum.

In one embodiment, the starting liver cell population is obtained from a mammal. In one embodiment, the starting liver cell population was previously isolated from a mammal.

A method for identifying molecular probes specific for somatic liver stem cells is provided. The method comprises culturing and expanding said single somatic liver stem cells using the method of culturing and expanding somatic liver stem cells in vitro described above, and using said population of expanded somatic liver stem cells for comparison to a second population of non-stem cells to identify differences in gene and/or protein expression between the two said populations.

A method of culturing and expanding somatic liver stem cells ex vivo is further provided that comprises culturing somatic liver stem cells isolated from a mammal in a culture medium which permits cell growth under conditions, and for a time sufficient, to permit cell growth, wherein the expression of a protein downstream of the guanine nucleotide biosynthesis pathway in said somatic liver stem cells is modulated by an agent present in the culture medium or by a genetic manipulation to said somatic liver stem cells such that asymmetric cell kinetics are suppressed.

In one embodiment, the method of culturing and expanding somatic liver stem cells ex vivo comprises culturing a starting liver cell population containing said somatic liver stem cells to confluence and culturing said somatic liver stem cells in a culture medium which permits cell growth under conditions, and for a time sufficient, to permit cell growth, wherein the expression of a protein downstream of the guanine nucleotide biosynthesis pathway in said somatic liver stem cells is modulated by an agent present in the culture medium or by a genetic manipulation to said somatic liver stem cells such that asymmetric cell kinetics are suppressed.

In one embodiment, the starting liver cell population containing said somatic liver stem cells is cultured to confluence in media supplemented with TGF-β and EGF. In one embodiment, the starting liver cell population containing said somatic liver stem cells is cultured to confluence in media that contains about 1% serum.

In one embodiment, the modulation is increased expression of the protein.

In one embodiment, the modulation is decreased expression of the protein.

A method for treating liver disease is provided. The method comprises administering to a subject a composition that stimulates liver stem cells to replicate by converting from asymmetric cell kinetics to symmetric cell kinetics resulting in enhanced proliferation of said liver stem cells with a reversibly reduced production of differentiating progeny cells.

In one embodiment, the agent that stimulates conversion of the stem cells from asymmetric cell kinetics to symmetric cell kinetics is a guanine nucleotide precursor (GNPr), a analogue or derivative thereof.

In one embodiment, the guanine nucleotide precursor is xanthosine or hypoxanthine.

In one embodiment, the composition is administered parenterally.

In one embodiment, the guanine nucleotide precursor is present in an amount of 10-10,000 μM.

In one embodiment, the guanine nucleotide precursor is present in an amount of 50-1,500 μM.

A composition comprising a population of human somatic liver stem cells, wherein the population contains at least 100 human somatic liver stem cells is also provided.

In one embodiment, the composition comprises at least 60% multi-potent somatic liver stem cells.

In one embodiment, the population contains more than 1,000 multi-potent liver stem cells.

In one embodiment, the composition is at least 60% multi-potent liver stem cells.

In one embodiment, the composition of human somatic liver stem cells comprise a cytochrome P450 promoter operably linked to a reporter gene. In a further embodiment, the cytochrome P450 promoter is the CYP3A4 promoter.

In one embodiment, the composition is a human hepatic stem cell strain obtained by the above method further comprising a cytochrome P450 promoter operably linked to a reporter gene.

As used herein, somatic liver stem cells derived from adult tissues are sometimes referred to as somatic stem cells, or hepatic stem cells, or liver stem cells, or adult stem cells, or post-natal stem cells, or simply as stem cells. Somatic liver stem cells include any stem cell isolated from the liver. These include, but are not limited to hepatoblasts, hepatic progenitor cells or biliary cells, preferably biliary epithelial cells. The hepatoblast is a multi-potential cell which has the capacity to differentiate to hepatocytes, biliary cells or pancreatic cells. As used herein a stem cell is multi-potent and can give rise to a number of different cells, at least two different cells, more preferably at least three different cells, in contrast to differentiated cells. These include, but are not limited to, the multi-potent stem cells that gives rise to hepatocytes and bile duct cells, the major cellular components of the liver.

Adult somatic stem cells predominantly divide by asymmetric cell kinetics (see FIG. 1). While somatic stem cells also undergo limited symmetric divisions (that produce two identical stem cells) in developing adult tissues, such symmetric kinetics are restricted to periods of tissue expansion and tissue repair. Inappropriate symmetric somatic stem cell divisions evoke mechanisms leading to apoptosis of duplicitous stem cells (Potten and Grant, 1998). Some stem cells may also lie dormant for long periods before initiating division in response to specific developmental cues, as in reproductive tissues like the breast. However, the predominant cell kinetics state of somatic stem cells is asymmetric (Cairns, 1975; Poldosky, 1993; Loeffler and Potten, 1997).

During asymmetric cell kinetics, one daughter cell divides with the same kinetics as its stem cell parent, while the second daughter gives rise to a differentiating non-dividing cell lineage. The second daughter may differentiate immediately; or depending on the tissue, it may undergo a finite number of successive symmetric divisions to give rise to a larger pool of differentiating cells. The second daughter and its dividing progeny are called transit cells (Loeffler and Potten, 1997). Transit cell divisions ultimately result in mature, differentiated, terminally arrested cells. In tissues with high rates of cell turnover, the endpoint for differentiated terminal cells is programmed cell death by apoptosis.

Asymmetric cell kinetics evolved in vertebrates as a mechanism to insure tissue cell renewal while maintaining a limited set of stem cells and constant adult body mass. Mutations that disrupt asymmetric cell kinetics are an absolute requirement for the formation of a clinically significant tumor mass (Cairns, 1975). In many ways, asymmetric cell kinetics provide a critical protective mechanism against the emergence of neoplastic growths that are life threatening.

Figure 2:
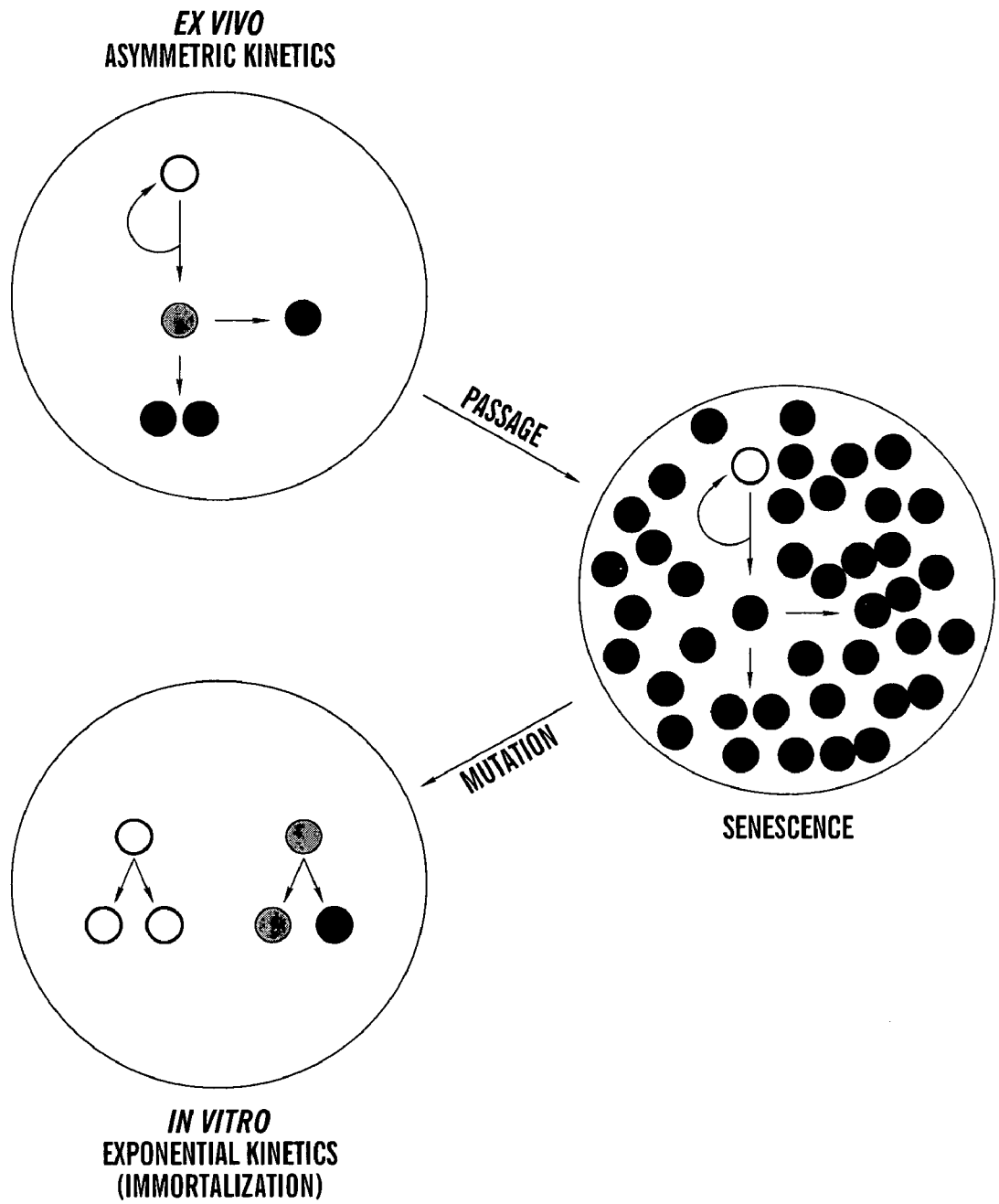
FIG. 2 depicts a cell kinetics barrier to the expansion of somatic stem cells in vitro. Of explanted tissue cells, somatic stem cells (bold-lined, open circles) have the capacity for long-term division ex vivo. However, if they retain even a rudimentary form of their in vivo asymmetric cell kinetics program, in vitro, their numbers will not increase. Instead, they will be diluted by the continuous accumulation of cells in terminal arrest lineages (closed circles). Continuous passage of cultures will result in "senescence" as a kinetics endpoint. In order to establish an immortal cell line, mutations must occur that either interfere with the maturation of terminal cells (immature terminal cells, thin-lined open circles) or that convert stem cells to symmetric exponential kinetics, in which only stem cells are produced. If asymmetric stem cell kinetics were suppressed, this model predicts that stem cells could be expanded in culture with fewer growth-activating mutations, like p53 mutations. P53 mutations relieve repression of IMPDH expression.

In culture, continued asymmetric cell kinetics of explanted cells are a major obstacle to their expansion in vitro (FIG. 2). Ongoing asymmetric kinetics results in dilution and loss of an initial relatively fixed number of stem cells by the accumulation of much greater numbers of their terminally differentiating progeny. If a sample includes both exponentially growing cells as well as somatic stem cells, the growth of the exponentially growing cells will rapidly overwhelm the somatic stem cells, leading to their dilution.

Figure 1B:
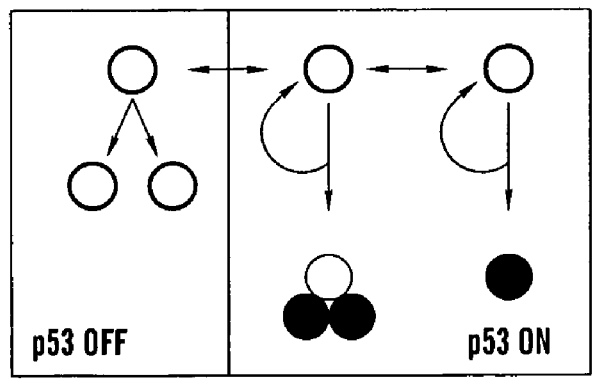

One regulator of asymmetric cell kinetics is the p53 tumor suppressor protein. Several stable cultured murine cell lines have been derived that exhibit asymmetric cell kinetics in response to controlled expression of the wild-type murine p53 (FIG. 1B). (Sherley, 1991; Sherley et al, 1995 A-B; Liu et al., 1998 A-B; Rambhatla et al., 2001).

The p53 model cell lines have been used to define cellular mechanisms that regulate asymmetric cell kinetics. In addition to p53, the rate-limiting enzyme of guanine nucleotide biosynthesis, inosine-5'-monophosphate dehydrogenase (IMPDH) is an important determinant of asymmetric cell kinetics. IMPDH catalyzes the conversion of IMP to xanthosine monophosphate (XMP) for guanine nucleotide biosynthesis. This enzymatic reaction is rate-determining for the formation of the next metabolite in the pathway, GMP, from which all other cellular guanine nucleotides are derived.

Accordingly, high levels of GNPs promote exponential kinetics, whereas low levels of GNPs promote asymmetric cell kinetics. The present invention provides methods for expanding somatic liver stem cells ex vivo by enhancing guanine nucleotide biosynthesis, thereby expanding cellular pools of GNPs and conditionally suppressing asymmetric cell kinetics.

According to methods of the invention, expansion of the human multi-potent somatic liver stem cells can start with only a single cell. Preferably, one can start with a composition containing only 1% human multi-potent somatic liver stem cells. These multi-potent human liver stem cells can be enriched up to at least 30%, for example at least 40%, 50%, 60%, 70%, 80%, 90%, 95% of the entire composition because of the suppression of asymmetric cell kinetics.

Mechanisms which function downstream of the GNPs to regulate cell kinetics (i.e. asymmetric v. symmetric) can also be used to conditionally suppress asymmetric cell kinetics thereby effectively permitting a greater percent of expression by the stem cell. These mechanisms include both genetic and/or pharmacological approaches, analogous to those described in detail herein. For example, one can enhance expression of a protein downstream of the GNP biosynthesis pathway, if that protein inhibits asymmetric cell kinetics. Alternatively, one can downregulate expression of a protein downstream of the GNP pathway if it promotes asymmetric cell kinetics.

Pharmacological Methods for Stem Cell Expansion

In the pharmacological method of the present invention, somatic liver stem cells are cultivated in the presence of compounds which enhance guanine nucleotide biosynthesis. This expands guanine nucleotide pools, which in turn suppress the undesired asymmetric cell kinetics thereby permitting expansion of stem cells resulting in production of a greater percent of stem cells. Preferably, the compounds are guanine nucleotide precursors (GNPrs, including rGNPrs). More preferably, the GNPr has a xanthine nucleus, such as xanthosine (Xs), xanthine (Xn) or hypoxanthine (Hx). More preferably the GNPr is xanthosine, xanthine, or hypoxanthine. Even more preferably, the GNPr is xanthine or xanthosine, most preferably the GNPr is xanthosine. These compounds can be used at effective concentrations ranging from 1 uM to 10 mM or 1 uM to 5 mM. Preferably the concentration ranges from 10 uM to 1.5 mM. More preferably the concentration is in the range of 50 uM to 5 mM or 50 uM to 1500 μm or one can use any range contained therein. In one preferred embodiment, cells are cultured in the presence of 1.5 mM xanthosine. One skilled in the art can determine the effective concentration necessary to expand guanine nucleotide pools and suppress asymmetric kinetics of the liver stem cell to be propagated.

Genetic Methods for Liver Stem Cell Expansion

In one embodiment of the invention, genes that lead to constitutive upregulation of guanine nucleotides (GNPs), including guanine ribonucleotides (rGNPs), are introduced into the somatic liver stem cells. Preferred genes are those that encode inosine-5'monophosphate dehydrogenase (IMPDH) or xanthine phosphoribosyltransferase (XPRT), or other genes which have the same biochemical effect. More preferably, the gene is XPRT. While there are currently no known mammalian forms of XPRT, and its substrate xanthine is present in very low levels in mammalian cells, the activity of the transgenic XPRT can be regulated by supplying xanthine exogenously. As explained below, it is preferred that the genes are operably linked to an inducible promoter.

In another embodiment of the invention, transgenic animals are generated with introduced genes that lead to constitutive upregulation of GNPs, including rGNPs. Methods for making transgenic animals are well known to those skilled in the art and any such method can be used.

In one preferred embodiment, the transgene introduced into the animal is the gene encoding for xanthine phosphoribosyltransferase (XPRT), for example from the protozoan *Leishmania donovani*. The XPRT enzyme can convert xanthine into xanthosine monophosphate, the critical precursor for cellular guanine nucleotides. This enzyme has no mammalian counterpart and its substrate can enter the cell via ubiquitously expressed nucleobase transporters. Therefore, one can control the kinetics of adult stem cells expressing XPRT that are derived from the transgenic animal by supplementing with or depriving the culture medium of xanthine. In the presence of xanthine, XPRT-expressing cells increase their cellular level of guanine nucleotides independently of their normal endogenous pathway involving the conversion of inosine monophosphate to xanthosaine monophosphate by the enzyme inosine monophosphate dehydrogenase. Preferably, the transgene is operably linked to an inducible promoter.

As used herein, the introduction of DNA into a host cell is referred to as transduction, sometimes also known as transfection or infection. Stem cells can be transduced ex vivo at high efficiency.

As used herein, the terms "transgene", "heterologous gene", "exogenous genetic material", "exogenous gene" and "nucleotide sequence encoding the gene" are used interchangeably and meant to refer to genomic DNA, cDNA, synthetic DNA and RNA, mRNA and antisense DNA and RNA, and sRNAs, miRNAs and RNAi's, which are introduced into the stem cell. The exogenous genetic material may be heterologous or an additional copy or copies of genetic material normally found in the individual or animal. When cells are to be used as a component of a pharmaceutical composition in a method for treating human diseases, conditions or disorders, the exogenous genetic material that is used to transform the cells may also encode proteins selected as therapeutics used to treat the individual and/or to make the cells more amenable to transplantation.

An expression cassette can be created for expression of the gene that leads to constitutive upregulation of guanine nucleotides, including guanine ribonucleotides. Such an expression cassette can include regulatory elements such as a promoter, an initiation codon, a stop codon, and a polyadenylation signal. It is necessary that these elements be operable in the stem cells or in cells that arise from the stem cells after infusion into an individual. Moreover, it is necessary that these elements be operably linked to the nucleotide sequence that encodes the protein such that the nucleotide sequence can be expressed in the stem cells and thus the protein can be produced. Initiation codons and stop codons are generally considered to be part of a nucleotide sequence that encodes the protein.

A variety of promoters can be used for expression of the transgene. Promoters that can be used to express the gene are well known in the art. Promoters include cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter and the herpes simplex tk virus promoter. For example, one can use a tissue specific promoter, i.e. a promoter that functions in some tissues but not in others. Such promoters include EF2 responsive promoters, etc. Regulatable promoters are preferred. Such systems include those using the lac repressor from *E. coli* as a transcription modulator to regulate transcription from lac operator-bearing mammalian cell promoters (Brown, M. et al., *Cell*, 49:603-612 (1987)), those using the tetracycline repressor (tetR) (Gossen, M., and Bujard, H., *Proc. Natl. Acad. Sci. USA* 89:5547-5551 (1992); Yao, F. et al., *Human Gene Therapy*, 9:1939-1950 (1998); Shockelt, P., et al., *Proc. Natl. Acad. Sci. USA*, 92:6522-6526 (1995)). Other systems include FK506 dimer, VP16 or p65 using astradiol, RU486, diphenol murislerone or rapamycin. Inducible systems are available from Invitrogen, Clontech and Ariad. Systems using a repressor with the operon are preferred. Regulation of transgene expression in target cells represents a critical aspect of gene therapy. For example, the lac repressor from *Escherichia coli* can function as a transcriptional modulator to regulate transcription from lac operator-bearing mammalian cell promoters (M. Brown et al., *Cell*, 49:603-612 (1987)); Gossen and Bujard (1992); (M. Gossen et al., *Natl. Acad. Sci. USA*, 89:5547-5551 (1992)) combined the tetracycline repressor (tetR) with the transcription activator (VP16) to create a tetR-mammalian cell transcription activator fusion protein, tTa (tetR-VP16), with the tetO-bearing minimal promoter derived from the human cytomegalovirus (hCMV) major immediate-early promoter to create a tetR-tet operator system to control gene expression in mammalian cells. Recently Yao and colleagues (F. Yao et al., Hum Gene Ther. September 1; 9(13):1939-50 (1998)). demonstrated that the tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter. One particular advantage of this tetracycline inducible switch is that it does not require the use of a tetracycline repressor-mammalian cells transactivator or repressor fusion protein, which in some instances can be toxic to cells (M. Gossen et al., *Natl. Acad. Sci. USA*, 89:5547-5551 (1992); P. Shockett et al., *Proc. Natl. Acad. Sci. USA*, 92:6522-6526 (1995)), to achieve its regulatable effects.

The effectiveness of some inducible promoters increases over time. In such cases one can enhance the effectiveness of such systems by inserting multiple repressors in tandem, e.g. TetR linked to a TetR by an IRES. Alternatively, one can wait at least 3 days before screening for the desired function. While some silencing may occur, it is minimized given the large number of cells being used, preferably at least $1 \times 10^4$, more preferably at least $1 \times 10^5$, still more preferably at least $1 \times 10^6$, and even more preferably at least $1 \times 10^7$, the effect of silencing is minimal. One can enhance expression of desired proteins by known means to enhance the effectiveness of this system. For example, using the Woodchuck Hepatitis Virus Posttranscriptional Regulatory Element (WPRE). See Loeb, V. E., et al., *Human Gene Therapy* 10:2295-2305 (1999); Zufferey, R., et al., *J. of Virol.* 73:2886-2892 (1999); Donello, J. E., et al., *J. of Virol.* 72:5085-5092 (1998).

Examples of polyadenylation signals useful to practice the present invention include but are not limited to human collagen I polyadenylation signal, human collagen II polyadenylation signal, and SV40 polyadenylation signal.

In order to maximize protein production, codons may be selected which are most efficiently translated in the cell. The skilled artisan can prepare such sequences using known techniques based upon the present disclosure.

The exogenous genetic material that includes the transgene operably linked to the regulatory elements may remain present in the cell as a functioning cytoplasmic molecule, a functioning episomal molecule or it may integrate into the cell's chromosomal DNA. Exogenous genetic material may be introduced into cells where it remains as separate genetic material in the form of a plasmid. Alternatively, linear DNA, which can integrate into the chromosome, may be introduced into the cell. When introducing DNA into the cell, reagents, which promote DNA integration into chromosomes, may be added. DNA sequences, which are useful to promote integration, may also be included in the DNA molecule. Alternatively, RNA may be introduced into the cell.

Selectable markers can be used to monitor uptake of the desired gene. These marker genes can be under the control of any promoter or an inducible promoter. These are well known in the art and include genes that change the sensitivity of a cell to a stimulus such as a nutrient, an antibiotic, etc. Genes include those for neo, puro, tk, multiple drug resistance (MDR), etc. Other genes express proteins that can readily be screened for such as green fluorescent protein (GFP), blue fluorescent protein (BFP), luciferase, LacZ, nerve growth factor receptor (NGFR), etc.

For example, one can set up systems to screen liver stem cells automatically for the marker. In this way one can rapidly select transduced liver stem cells from non-transformed cells. For example, the resultant particles can be contacted with about one million cells. Even at transduction rates of 10-15% one will obtain 100-150,000 cells. An automatic sorter that screens and selects cells displaying the marker, e.g. GFP, can be used in the present method.

When the transgene is XPRT, cells expressing XPRT will be resistant to cytotoxic IMPDH inhibitors such as mycophenolic acid in the presence of xanthine. Thus, transduced liver stem cells can be selected from non-transformed cells by culturing transfectants in the presence of an IMPDH inhibitor (such as mycophenolic acid) and xanthine. One can use other markers to readily select transduced cells.

Vectors include chemical conjugates, plasmids, phage, etc. The vectors can be chromosomal, non-chromosomal or synthetic. Commercial expression vectors are well known in the art, for example pcDNA 3.1, pcDNA4 HisMax, pACH, pMT4, PND, etc. Preferred vectors include viral vectors, fusion proteins and chemical conjugates. Retroviral vectors include Moloney murine leukemia viruses and pseudotyped lentiviral vectors such as FIV or HIV cores with a heterologous envelope. Other vectors include pox vectors such as orthopox or avipox vectors, herpesvirus vectors such as a herpes simplex I virus (HSV) vector (Geller, A. I. et al., (1995), *J. Neurochem,* 64: 487; Lim, F., et al., (1995) in *DNA Cloning: Mammalian Systems*, D. Glover, Ed., Oxford Univ. Press, Oxford England; Geller, A. I. et al. (1993), *Proc Natl. Acad. Sci.*: U.S.A. 90:7603; Geller, A. I., et al., (1990) *Proc Natl. Acad. Sci USA* 87:1149), adenovirus vectors (LeGal LaSalle et al. (1993), *Science,* 259:988; Davidson, et al. (1993) *Nat. Genet* 3: 219; Yang, et al., (1995) *J. Virol.* 69: 2004) and adeno-associated virus vectors (Kaplitt, M. G., et al. (1994) *Nat. Genet.* 8: 148).

The introduction of the gene into the stem cell can be by standard techniques, e.g. infection, transfection, transduction or transformation. Examples of modes of gene transfer include e.g., naked DNA, CaPO$_4$ precipitation, DEAE dextran, electroporation, protoplast fusion, lipofection, cell microinjection, and viral vectors, adjuvant-assisted DNA, gene gun, catheters, etc.

The vectors are used to transduce the liver stem cells ex vivo. One can rapidly select the transduced cells by screening for the marker. Thereafter, one can take the transduced cells and grow them under the appropriate conditions or insert those cells into a host animal.

Somatic Liver Stem Cells

The liver stem cells of the present invention may be isolated from tissue of an adult mammal, preferably a human. The cells include cells which generate daughter cells that can mature through the liver lineage and offer the entire range of liver functions, for example cells that produce hepatocytes, cholangiocytes and bile duct cells.

The methods of ex vivo propagation described herein can be applied to any liver stem cell whether it be muti-potent, pluripotent, or a unique progenitor subtype, such as a stem cell that produces only hepatocytes or a subtype that produces bile duct cells. Parenchymal cells (epithelial or epitheloid cells) are morphologically homogeneous and consist of small cells with scant cytoplasm and, therefore, high nuclear to cytoplasmic ratios, with undifferentiated, pale, nuclei and a few intercellular adhesions. Most liver parenchymal cells at this stage are considered to be bipotent for bile duct cells and hepatocytes. Although they express, usually weakly, some liver-specific functions known to be activated very early in development, such as albumin and alpha-fetoprotein (AFP), they do not express adult-specific markers such as glycogen, urea-cycle enzymes or major urinary protein (MUP). Only a few islands of fetal cells are positive for BDS a bile duct cell-specific marker, and none are positive for HES, a hepatocyte-specific marker (see Germain et al., Cancer Research, Vol. 48, pp. 4909-4918 (1988)). Preferably, the liver stem cells are isolated from the non-parenchymal cell fraction of liver cells.

The somatic liver stem cells act as precursor cells, which produce daughter cells that mature into differentiated liver cells. The liver stem cells can be isolated from the individual in need of liver stem cell therapy, or from another individual. Preferably, the individual is a matched individual to insure that rejection problems do not occur. Those having ordinary skill in the art can readily identify matched donors using standard techniques and criteria. Other therapies to avoid rejection of foreign cells are known in the art. For example, somatic liver stem cells may be immune-privileged, so the graft versus host disease after allogenic transplant may be minimal or non-existent (Weissman, 2000). Liver stem cells from a matched donor may be administered by any known means, for example, intravenous injection, or injection directly into the liver or surrounding tissue.

Cells can be obtained from donor liver tissue by dissociation of individual cells from the connecting extracellular matrix of the tissue. Tissue is removed using a sterile procedure, and the cells are dissociated using any method known in the art including treatment with enzymes such as trypsin, collagenase, and the like, or by using physical methods of dissociation such as with a blunt instrument.

In one preferred embodiment, the liver stem cells are surgically removed from a patient and the non-parenchymal cell fraction is used to isolate liver stem cells.

Any medium can be used that is capable of supporting cell growth, including HEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. Serum can contain xanthine, hypoxanthine, or other compounds which enhance guanine nucleotide biosynthesis, although generally at levels below the effective concentration to suppress asymmetric cell kinetics. Thus, preferably a defined, serum-free culture medium is used, as serum contains unknown components (i.e. is undefined). Preferably, if serum is used, it has been dialyzed to remove GNPrs, including rGNPrs. A defined culture medium is also preferred if the cells are to be used for transplantation purposes. A particularly preferable culture medium is a defined culture medium comprising a mixture of DMEM and a defined hormone and salt mixture. As indicated herein, by including a compound such as a GNPr, including rGNPrs, asymmetric cell kinetics are suppressed. Thus, the effect of division by differentiated transit cells, which results in the diluting of the liver stem cells, is reduced.

The culture medium can be supplemented with a proliferation-inducing growth factor(s). As used herein, the term "growth factor" refers to a protein, peptide or other molecule having a growth, proliferative, differentiative, or trophic effect on cells in general, including stem cells, e.g., liver stem cells. Growth factors that may be used include any trophic factor that allows liver stem cells to proliferate like other cells, including any molecule that binds to a receptor on the surface of the cell to exert a trophic, or growth-inducing effect on the cell. Preferred proliferation-inducing growth factors include EGF, TGF-β1, amphiregulin, acidic fibroblast growth factor (aFGF or FGF-1), basic fibroblast growth factor (bFGF or FGF-2), transforming growth factor alpha (TGF-alpha), and combinations thereof. Growth factors are usually added to the culture medium at concentrations ranging between about 1 fg/ml to 1 mg/ml. Concentrations between about 1 to 100 ng/ml are usually sufficient. Simple titration experiments can be easily performed to determine the optimal concentration of a particular growth factor. In one preferred embodiment, Epidermal growth factor (e.g., 20 ng/ml) and TGF-β1 (e.g., 0.5 ng/ml) are used.

In addition to proliferation-inducing growth factors, other growth factors may be added to the culture medium that influence proliferation and differentiation of the cells including NGF, platelet-derived growth factor (PDGF), thyrotropin releasing hormone (TRH), transforming growth factor betas (TGFβs), insulin-like growth factor (IGF-1) and the like. Differentiation can also be induced by growing cells to confluncey.

Liver stem cells can be cultured in suspension or on a fixed substrate. For example, the stem cells can be grown on a hydrogel, such as a peptide hydrogel, as described below. Alternatively, the stem cells can be propagated on tissue culture plates or in suspension cultures. Cell suspensions can be seeded in any receptacle capable of sustaining cells, particularly culture flasks, cultures plates, or roller bottles, more particularly in small culture flasks such as 25 cm$^2$ cultures flasks. Preferably, the liver stem cells are grown on tissue culture plates. In one preferred embodiment, cells are cultured at high cell density to promote the suppression of asymmetric cell kinetics.

Conditions for culturing should be close to physiological conditions. The pH of the culture medium should be close to physiological pH, preferably between pH 6-8, more preferably between about pH 7 to 7.8, with pH 7.4 being most preferred. Physiological temperatures range between about 30° C. to 40° C. Cells are preferably cultured at temperatures between about 32° C. to about 38° C., and more preferably between about 35° C. to about 37° C.

Cells are preferably cultured for 3-30 days, preferably at least about 7 days, more preferably at least 10 days, still more preferably at least about 14 days. Cells can be cultured substantially longer. They can also be frozen using known methods such as cryopreservation, and thawed and used as needed.

Another preferred embodiment provides for deriving clonal lines of somatic liver stem cells by limiting dilution plating or single cell sorting. Methods for deriving clonal cell lines are well known in the art and are described for example in Puck et al., 1956; Nias et al., 1965; and Leong et al., 1985. See also Example II.

Uses of Expanded Somatic Liver Stem Cells

The present invention also provides for the administration of expanded populations of liver stem cells to a patient in need thereof. The term "administration" as used herein refers to well recognized forms of administration, such as intravenous or injection, as well as to administration by transplantation, for example transplantation by grafting or transplantation of tissue engineered liver derived from liver stem cells.

The expanded liver stem cells of the present invention can be used for a variety of purposes, including, but not limited, cell replacement therapies in order to treat for example, chronic and acute liver failure or disease; tissue engineering applications, such as their use in generation of functional artificial liver or grafts; drug discovery applications (e.g. toxicology studies and metabolic profiling); and in gene therapy applications.

The expanded liver stem cells of the invention are also particularly useful for facilitating research on liver stem cell biology and differentiation.

In one preferred embodiment, autologous liver stem cells are used to replace injured cells in order to produce functional liver tissue. The use of autologous liver stem cells reduces the need for immune suppression interventions upon transplant.

Transplantation of tissue engineered artificial grafts with newly introduced liver stem cells, is particularly useful for treatment of chronic and acute liver disease.

In one preferred embodiment, individual liver stem cells can be introduced into the liver by injection.

Gene Delivery Applications

According to the invention, in addition to the introduction of genes that lead to constitutive upregulation of guanine nucleotides, including guanine ribonucleotides, the liver stem cells can be further genetically altered prior to reintroducing the cells into the individual for gene therapy, to introduce a gene whose expression has therapeutic effect on the individual.

For example, the liver cells may have a defective gene that inhibits proper liver function. By introducing normal genes in expressible form, individuals suffering from liver dysfunction can be provided the means to compensate for genetic defects and eliminate, alleviate or reduce some or all of the symptoms of the deficiency.

A vector can be used for expression of the transgene encoding a desired wild type hormone or a gene encoding a desired mutant hormone. Preferably, as described above, the transgene is operably linked to regulatory sequences required to achieve expression of the gene in for example the liver stem cell or the cells that arise from the liver stem cells, such as hepatic cells or bile duct cells after they are infused into an individual. Such regulatory sequences include a promoter and a polyadenylation signal. The vector can contain any additional features compatible with expression in stem cells or their progeny, including for example selectable markers.

Administration of Expanded Liver Stem Cells

The methods of the invention involve administering the expanded liver stem cells to an individual by standard means, such as intravenous infusion and mucosal injection, as well as administration to an individual by transplantation. Transplantation techniques are well known to those skilled in the art and include surgical and grafting techniques.

In one preferred embodiment, liver stem cells are introduced into a liver or graft by injection.

In another embodiment, the liver stem cells are used to engineer liver either alone or in the presence of additional stem cell niche components, such as extracellular matrix. The newly engineered liver is then transplanted into an individual by surgical means.

The discovery that isolated stem cells may be expanded ex vivo and administered intravenously provides the means for systemic administration. In certain applications, such as gene therapeutic methods, systemic administration by intravenous infusion may be desired. In a preferred embodiment, the stem cells are administered to an individual by infusion into the superior mesenteric artery or celiac artery. In another preferred embodiment, the stem cells are administered to an individual by infusion into the peritoneal cavity with subsequent migration of cells via subdiaphragmatic lymphatics, infusion into the subclavian vein via the thoracic duct, infusion into the heart via the superior vena cava and directly into liver sites via infusion into the hepatic arterial blood supply. The stem cells may also be delivered locally by irrigation down the recipient's airway or by direct injection into the mucosa of the intestine.

After isolating the liver stem cells, the cells can be administered after a period of time sufficient to allow them to convert from asymmetric cell kinetics to exponential kinetics, typically after they have been cultured from 1 day to over a year. Preferably the cells are cultured for 3-30 days, more preferably 4-14 days, most preferably at least 7 days.

In one embodiment of the invention, the stem cells can be induced to differentiate following expansion in vitro, prior to administration to the individual. Preferably, the pool of guanine nucleotides, including guanine ribonucleotides, is decreased at the same time differentiation is induced, for example by removal of the GNPr, including removal of the rGNPr, from the culture medium (if a pharmacological approach has been used) or by downregulating expression of the transgene.

Differentiation of the liver stem cells can be induced by any method known in the art which activates the cascade of biological events which lead to cell cycle arrest, which include growth to confluence, growth factor withdrawal, addition of growth inhibitory factors, the liberation of inositol triphosphate and intracellular $Ca^{2+}$, liberation of diacyl glycerol and the activation of protein kinase C and other cellular kinases, and the like. Treatment with phorbol esters, differentiation-inducing growth factors and other chemical signals can induce differentiation. Differentiation can also be induced by plating the cells on a fixed substrate such as flasks, plates, or coverslips coated with an ionically charged surface such as poly-L-lysine and poly-L-ornithine and the like.

Other substrates may be used to induce differentiation such as collagen, fibronectin, laminin, MATRIGEL.™. (Collaborative Research), and the like. Differentiation can also be induced by leaving the cells in suspension in the presence of a proliferation-inducing growth factor, without reinitiation of proliferation.

Differentiation can be determined using immunocytochemistry techniques well known in the art. Immunocytochemistry (e.g. dual-label immunofluorescence and immunoperoxidase methods) utilizes antibodies that detect cell proteins to distinguish the cellular characteristics or phenotypic properties of differentiated cell types compared to markers present on liver stem cells.

For intravenous administration of liver stem cells, the isolated stem cells are removed from culture dishes, washed with saline, centrifuged to a pellet and resuspended in a glucose solution which is infused into the patient.

Between $10^4$ and $10^{13}$ cells per 100 kg person are administered per infusion. Preferably, between about $1\text{-}5\times10^4$ and $1\text{-}5\times10^7$ cells are infused intravenously per 100 kg person. More preferably, between about $1\times10^4$ and $5\times10^6$ cells are infused intravenously per 100 kg person. The cells can also be injected directly into the intestinal mucosa through an endoscope.

In some embodiments, a single administration of cells is provided. In other embodiments, multiple administrations are used. Multiple administrations can be provided over periodic time periods such as an initial treatment regime of 3-7 consecutive days, and then repeated at other times.

Another embodiment of the invention provides transgenic non-human animals into whose genome is stably integrated an exogenous DNA sequence comprising a constitutive promoter expressed in all cell types operably linked to a DNA sequence encoding a protein that leads to constitutive upregulation of guanine nucleotides, including the gene encoding inosine-5'-monophosphate dehydrogenase (IMPDH) or xanthine phophoribosyl transferase (XPRT). Preferably, the transgene is XPRT. Preferably, the transgenic animal is a mammal such as a mouse, rat or sheep.

The term "animal" here denotes all mammalian animals except humans. It also includes an individual animal in all stages of development, including embryonic and fetal stages. A "transgenic" animal is any animal containing cells that bear genetic information received, directly or indirectly, by deliberate genetic manipulation at the subcellular level, such as by microinjection or infection with recombinant virus.

"Transgenic" in the present context does not encompass classical crossbreeding or in vitro fertilization, but rather denotes animals in which one or more cells receive a recombinant DNA molecule. Although it is highly preferred that this molecule be integrated within the animal's chromosomes, the invention also encompasses the use of extrachromosomally replicating DNA sequences, such as might be engineered into yeast artificial chromosomes.

The term "germ cell line transgenic animal" refers to a transgenic animal in which the genetic information has been taken up and incorporated into a germ line cell, therefore conferring the ability to transfer the information to offspring. If such offspring, in fact, possess some or all of that information, then they, too, are transgenic animals.

The information to be introduced into the animal is preferably foreign to the species of animal to which the recipient belongs (i.e., "heterologous"), but the information may also be foreign only to the particular individual recipient, or genetic information already possessed by the recipient. In the last case, the introduced gene may be differently expressed than is the native gene.

The transgenic animals of this invention are other than human, and produce milk, blood serum, and urine. Farm animals (pigs, goats, sheep, cows, horses, rabbits and the like), rodents (such as mice), and domestic pets (for example, cats and dogs) are included in the scope of this invention. One preferred animal is a mouse. Mouse strains which are suitable for the derivation of transgenic mice as described herein are any common laboratory mouse strain. Preferred mouse strains to use for the derivation of transgenic mice founders of the present invention include FVB and C57 strains. Preferably, founder mice are bred onto wild-type mice to create lines of transgenic mice.

It is highly preferred that a transgenic animal of the present invention be produced by introducing into single cell embryos appropriate polynucleotides that encode XPRT or IMPDH, or fragments or modified products thereof, in a manner such that these polynucleotides are stably integrated into the DNA of germ line cells of the mature animal, and are inherited in normal mendelian fashion.

Advances in technologies for embryo micromanipulation now permit introduction of heterologous DNA into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a highly preferred method, developing embryos are infected with a retrovirus containing the desired DNA, and transgenic animals produced from the infected embryo. In a most preferred method, however, the appropriate DNAs are coinjected into the pronucleus or cytoplasm of embryos, preferably at the single cell stage, and the embryos allowed to develop into mature transgenic animals. Those techniques as well known. See reviews of standard laboratory procedures for microinjection of heterologous DNAs into mammalian fertilized ova, including Hogan et al., Manipulating the mouse embryo, (Cold Spring Harbor Press 1986); Krimpenfort et al., Bio/Technology 9:844 (1991); Palmiter et al., Cell, 41: 343 (1985); Kraemer et al., Genetic manipulation of the early mammalian embryo, Cold Spring Harbor Laboratory Press 1985; Hammer et al., Nature, 315: 680 (1985); Wagner et al., U.S. Pat. No. 5,175,385; Krimpenfort et al., U.S. Pat. No. 5,175,384, the respective contents of which are incorporated by reference. See also U.S. Pat. Nos. 4,736,866, 5,387,742, 5,545,806, 5,487,992, 5,489,742, 5,530,177, 5,523,226, 5,489,743, 5,434,340, and 5,530,179.

In another embodiment of the invention, a method is provided for treating liver disease. The method comprises administering to a subject a composition that stimulates conversion of liver stem cells from asymmetric cell kinetics to symmetric cell kinetics resulting in enhanced proliferation of liver stem cells with a reversibly reduced production of differentiating progeny cells.

In one preferred embodiment, the agent that stimulates conversion of the stem cells from asymmetric cell kinetics to symmetric cell kinetics is a guanine nucleotide precursor (GNPr), including a guanine ribonucleotide precursor (rGNPr), an analog or derivative thereof, such as xanthosine, hypoxanthine, or xanthine.

Any liver disease or liver failure can be treated by methods of the invention. Liver disease include, but are not limited to Hepatocellular Carcinoma, Alagille Syndrome, Alpha-1-Antitrypsin Deficiency, Autoimmune Hepatitis, Biliary Atresia, Chronic Hepatitis, Cancer of the Liver, Cirrhosis Liver Cysts Fatty Liver, Galactosemia Gilbert's Syndrome, Primary Biliary Cirrhosis, Hepatitis A, Hepatitis B, Hepatitis C, Primary Sclerosing Cholangitis, Reye's Syndrome, Sarcoidosis, Tyrosinemia, Type I Glycogen Storage Disease, Wilson's Disease, Neonatal Hepatitis, NonAlchoholic SteatoHepatitis, Porphyria, and Hemochromatosis.

The composition can be administered by any means known to those skilled in the art. In one embodiment the composition is administered parenterally, e.g. by injection.

The invention further provides for compositions comprising a population of human somatic liver stem cells. Such compositions can comprise a population of cells from 10-100,000, or more, of somatic liver stem cells. One can have any number of cells as part of the population including, but not limited to, 10, 20, 30, 40, 50, 100, 300, 500, 600, 800, 1,000 etc. cells in the composition.

In one embodiment, the composition is made up of at least 60% multi-potent somatic liver stem cells. In another embodiment, the composition is at least 70%, at least 75%, at least 80%, at least 85%, at least 90%, at least 95% or at least 99% multi-potent somatic liver stem cells.

A cell is multi-potent if it can still differentiate into at least two, preferably three other cells associated with the liver. The multi-potency of cells can be determined by methods well known to those skilled in the art and by using methods as described herein (e.g. monitor the expression of cytochrome p450 and other liver specific markers (Ck7, Ck8, CK19)).

Drug Discovery Applications (e.g. Toxicology Studies and Metabolic Profiling)

In one embodiment, one can create assays to look at compounds involved in liver metabolism. For example, induction of cytochrome P450 enzymes in liver hepatocytes is a key factor that determines the efficacy and toxicity of drugs. In particular, induction of P450s is an important mechanism of troublesome drug-drug interactions. Although methods exist for detection of drugs that inhibit specific P450 enzymes, thus far, until now, no approach has been available for high throughput assays to detect compounds that induce P450s.

Induction of P450s is the major cause of drug-drug interactions, and it is also an important factor that limits drug efficacy and governs drug toxicity. Cytochrome P450 induction assays have been difficult to develop, because they require intact normal human hepatocytes. These cells have proven intractable to production in numbers sufficient to sustain mass production of high throughput assays.

Herein, we describe the generation of human adult stem cell strains using the SACK method and provide a method that provides routine culture of stable, clonal human liver cell strains that retain the ability to express mature hepatocyte properties. These cell strains can be used to develop assays for liver drug metabolism, drug-induced hepatotoxicity, and detection of compounds. For example, compounds that induce expression of human cytochrome P450 CYP3A4 (CYP3A4 is responsible for the metabolism of 45%-60% of currently used drugs).

The hepatic stem cell strains of the invention (phHASC) provide an abundant, reliable source of cells with P450-induction properties of human adult hepatocytes which can be used in the development of high throughput assays for drug compounds.

In one embodiment a high throughput assays are developed that give an immediate real-time read-out of P450-induction using the cell strains of the invention. For example, hepatic stem cell strains with P450-induction properties can be stably-transfected with CYP3A4 promoter-fluorescent protein reporter gene constructs to develop a cell line for use in a high throughput assay to identify compounds that induce human P450s (See WO2006018270). For example, such an assay would involve addition of a compounds to the assay and, in one embodiment, a control assay to identify those compounds that modulate induction.

Cytochrome P450s, is the main focus of FDA Drug Evaluation Guidances (Guidances for Industry: Drug Metabolism/ Drug Interaction Studies in the Drug Development Process: Studies In Vitro, DHHS, U.S. FDA, April, 1997; Yuan et al., 2002). Together, cytochrome P450s CYP1A2, CYP2C9, CYP2D6, CYP2E1, CYP3A4 account for the P450 metabolism of ~99% of currently used drugs (Anzenbacher and Anzenbacherová, 2001). In addition, CYP1A1, CYP2A6, CYP2B6, CYP2C8, CYP2C19, CYP3A5, and CYP4A may also be evaluated, because FDA guidances also identify them as important liver enzymes for analysis (Yuan et al., 2002).

Genes for several proteins with intrinsic fluorescence are available for expression in mammalian cells. Examples with well-established track records as stable reporter proteins for gene transcription rate are green fluorescent protein (GFP), cyan fluorescent protein (CFP), and yellow fluorescent protein (YFP) (Heim et al., 1994; Tsien, 1998). Gene constructs that contain genes for these reporters under the control of well-defined promoters elements for transcriptionally-induced P450 enzymes can be stably introduced into phHASC strains.

The addition of P450 inducing compounds will lead to increased fluorescence in the test cell that can be detected and quantified either as a single endpoint analysis or by real-time fluorescence monitoring for greater specificity. The availability of multiple spectrally compatible fluorescent reporters permits one to monitor the simultaneous induction of multiple distinct P450 enzymes in the same cell.

The fluorescent reporter strategy is ideally suited as the detection basis for a high throughput assay for human P450 induction. The molecular basis for induction of many, if indeed not all, P450s is up-regulation of gene transcription induced by nuclear receptors that bind to P450 gene promoter elements as a consequence of interaction with endogenous and xenobiotic compounds (Quattrochi and Guzelian, 2001; Willson and Kliewer, 2002; Burk and Wojnowski, 2004). The gene regulatory sequences that confer drug-inducibility to the human CYP34A, a P450 of major clinical importance have been defined (Goodwin et al., 1999).

Because of the high success rate observed for SACK derivation of hHASC strains, it is possible to derive a panel of hHASC strains from individuals who differ in age, gender, and other clinically-relevant characteristics. This capability permits us to develop a panel of high throughput assays to determine the range of individual variability in P450-induction response.

EXAMPLES

Example 1

Propagation of Human Somatic Liver Stem Cells

Materials and Methods

Cells: Human liver cells are tested for blood borne agents, the non-parenchymal (NPC) fraction is place on ice for up to 24 hours and then centrifuged at 800×g for 5 minutes at 4° C. The resulting cell pellet is re-suspended in 50 ml-100 ml cold Dulbecco's Modified Eagle medium (DMEM-high glucose) supplemented with 1% dialyzed fetal bovine serum (DFBS). Based on the count of trypan blue-excluding viable cells, $5 \times 10^6$ viable cells are plated in 10-cm diameter cell culture dishes.

Initiation Culture Medium: DMEM-high glucose supplemented with 1% DFBS, 20 ng/ml recombinant human epidermal growth factor (EGF), 0.5 ng/ml transforming growth factor-β1 (TGF-β1), and one of the following purine compounds at 1 mM concentration (0.4 mM to 1.5 mM can also be used): Hypoxanthine, Xanthine, Xanthosine. Control cultures are without added purines and do not support establishment of cell strains.

Once a week, the culture medium is replaced with fresh medium of the same type.

After 2-7 weeks, cells are trypsinized from 4×10-cm diameter culture dishes and transferred in total into single wells of 24-well cell culture plates (2 cm²).

Maintenance Culture Medium: DMEM-high glucose supplemented with 10% DFBS, 20 ng/ml recombinant human epidermal growth factor, 0.5 ng/ml transforming growth factor β1, and the respective purine compound at the concentration used in the Initiation Culture Medium.

When the cell monolayers are nearly confluent, cells are trypsinized and transferred into one well of a 6-well cell culture plate. Thereafter, when nearly confluent, cells are transferred sequentially to a 25-cm² flask and a 75-cm² flask. Upon the next transfer (i.e., passage 5), a fraction of the cells are frozen in liquid nitrogen.

Freezing Medium: DMEM-high glucose supplemented with 10% DFBS, the respective purine, and 10% DMSO.

Freezing Procedure: Cells are pelleted and resuspended in Freezing Medium at approximately 1×10⁶ cells per ml and transferred to freezing vials. Vials were placed in an open plastic 0.45 caliber "bullet box" and chilled to −1° C. in a −20° C. freezer. At this point, vials were shaken to induce the ice transition and then transferred to −80° C. for 2 hours with the bullet box closed. Thereafter, vials were transferred to −140° C. for longterm storage.

Clonal Cell Strain Derivation: At passage 6, cells are plated at 300 cells per well in 6-well cell culture plates DMEM-high glucose supplemented with 10% DFBS, with respective purine supplementation, but no EGF or TGF-β1 supplementation. After 2 weeks of growth, individual cell colonies are transferred into single wells of 48-well culture plates (0.75 cm²), and the plated cells are cultured until they reach near confluency. Thereafter, cells are transferred sequentially to single wells of 12-well culture plates (3.8 cm²) and then split between two wells of a 6-well culture plate (9.6 cm²). The final clonal cell cultures are grown in the respective Maintenance Culture Medium supplemented with the respective purine, EGF, and TGF-β1.

Properties of Human Adult Liver Cell Strains

A colcemid arrest assay indicates that only 15%-25% of the cells are actively cycling, indicating the production of non-dividing cells. This conclusion is supported by data from analyses of the BrdU-labeling symmetry of paired sister cells. Fifteen percent of BrdU-labeled paired sister cells are found to divide asymmetrically, producing a cycling sister and a non-cycling sister. This property is diagnostic of adult stem cells.

Alpha fetal protein (AFP) and albumin are secreted by expanded cells under conditions that promote hepatocyte differentiation conditions (i.e., maintenance at confluency, at low serum concentration with EGF and TGF-beta supplementation).

The cell strains show increased rates of albumin and AFP secretion when cultured medium supplemented with human serum.

The detailed suppression of asymmetric cell kinetics (SACK) approach promotes expansion of adult human liver stem cell while limiting the growth of their differentiating progeny. No feeder layer is required to maintain the cells in culture, and currently no biological matrix is used. In previous studies investigating methods of expanding post-natal human liver cells, cultures could only be maintained for a few passages. Employing the SACK method, we have been able to maintain cultures for >20 passages thus far, corresponding to approximately 43 cell doublings. We have been able to derive 21 stable cultures from 7 livers, indicating a very robust method. Thus far, we have obtained a 35-fold expansion in cell number, corresponding to 7×10⁸ human liver cells for each expansion. We estimate that this represents about 1×10⁷ adult liver stem cells.

Suppression of Asymmetric Cell Kinetics (SACK) Strategy

Figure 3:
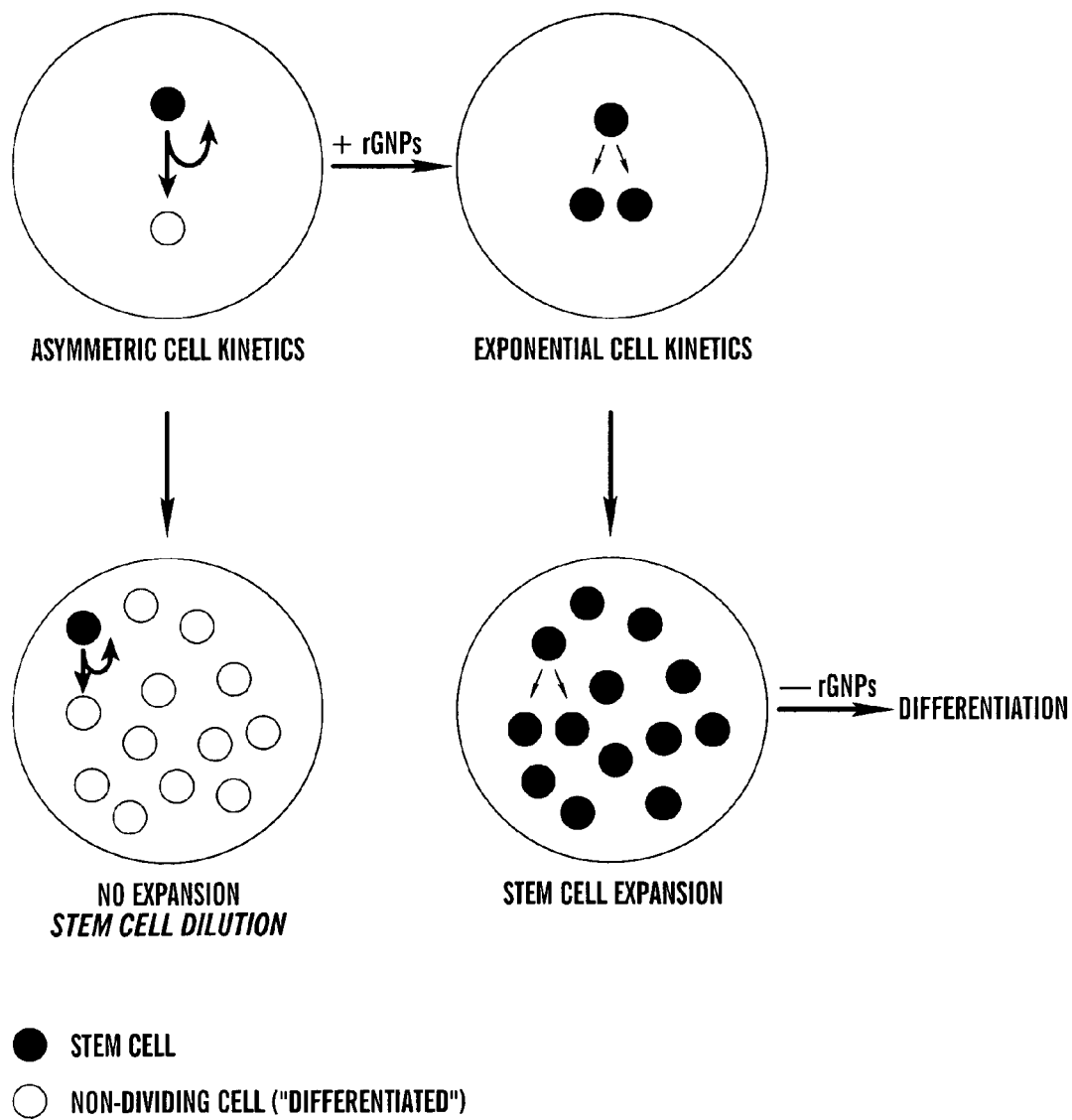
FIG. 3 depicts the effect of GNPs on cell kinetics. In the presence of GNPs, the liver stem cells undergo expansion having exponential cell kinetics whereas in the absence of GNPs there is asymmetric cell kinetics and stem cell dilution.
Figure 4:
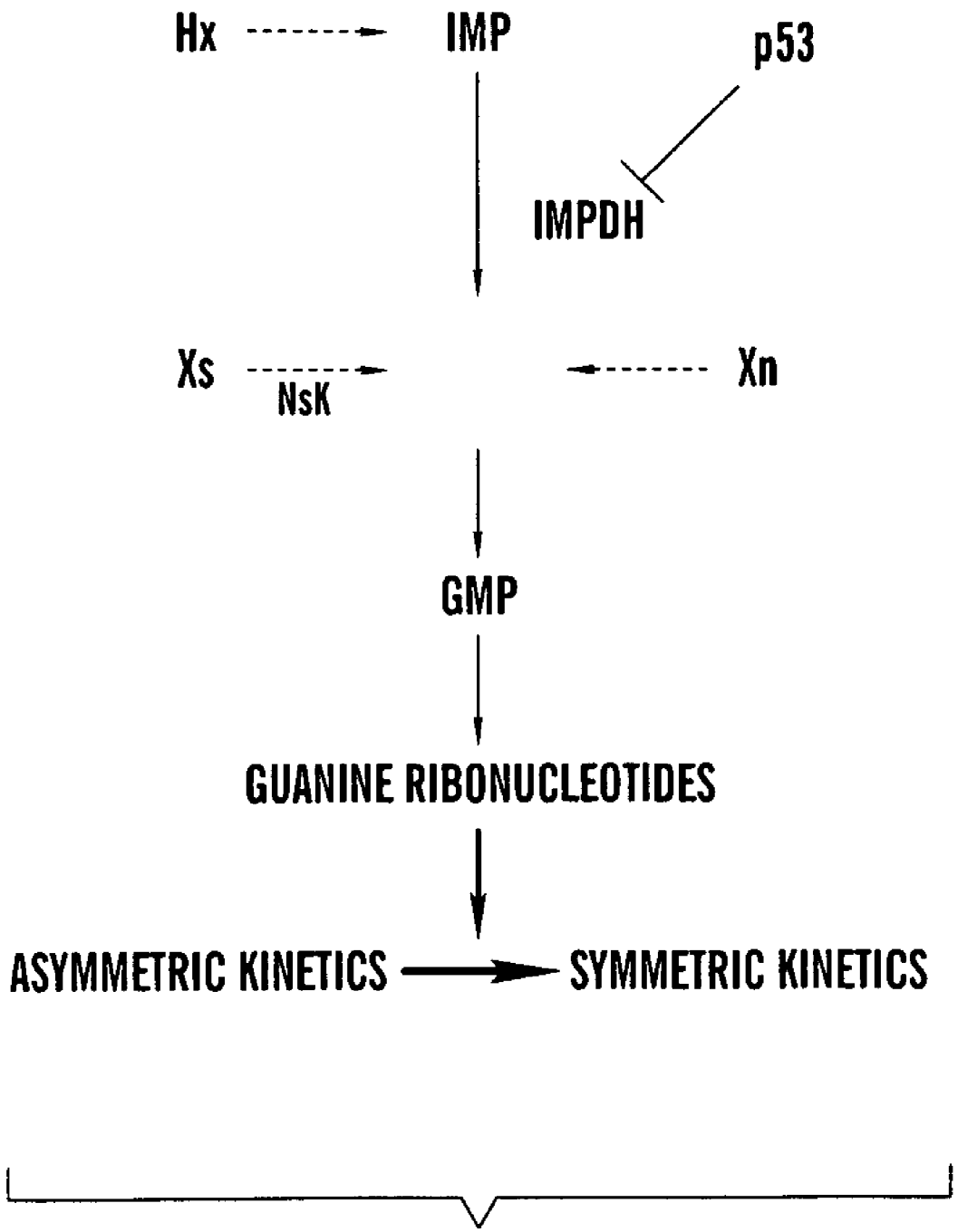
FIG. 4 shows the biochemical mechanism leading to symmetric kinetics. P53 expression induces asymmetric cell kinetics by leading to reduced guanine nucleotides. IMPDH=inosine monophosphate dehydrogenase; IMP=Inosine monophosphate; XMP=Xanthosine monophosphate; GMP=Guanosine monophosphate; Xn=Xanthine; Xs=Xanthosine; NsK=Nucleoside kinases; HGPRT=Hypoxanthine/guanine phosphoribosyl transferase.

Asymmetric cell kinetics are maintained by adult liver stem cells. When an adult stem cell divides asymmetrically, it give rise to one daughter cell that can divide further like the parent stem cell. The other daughter cell may differentiate immediately or do so after a finite number of divisions. We predicted that asymmetric cell kinetics is a major barrier in expanding adult somatic liver stem cells. As a result of asymmetric kinetics, in vitro, adult liver stem cells become diluted by more rapidly accumulating differentiated cells (FIG. 3). To overcome this limitation, we expanded adult somatic liver stem cells by increasing the levels of guanine nucleotide pools, including guanine ribonucleotide pools. As a result of increasing guanine nucleotide pools, including guanine ribonucleotide pool levels, adult liver stem cell kinetics shifts from asymmetric to symmetric, the latter which promotes exponential expansion of adult stem cells (FIG. 3). The addition of GNPs, including rGNPs, to the culture medium promotes the expansion of cellular guanine nucleotide pools (Sherley et al., 1995; Rambhatla et al., 2001; Merok and Sherley, 2001). The biochemical mechanism is depicted in FIG. 4.

We have used the SACK method to successfully expand hepatocytic and cholangiocytic stem cell strains from adult rat liver. To restrict the growth of non-stem cell types, we reduced serum supplementation and added EGF and TGF-β to induce the differentiation and growth arrest of non-stem cells. In contrast, previous analyses with SACK-derived rat hepatic adult stem cells showed them to be resistant to growth arrest under these conditions. With this modified SACK method, we show it is also possible to consistently establish juvenile and adult human liver cell cultures. In the presence of SACK compounds, these cultures have been maintained for over 6 months.

Figure 6A:
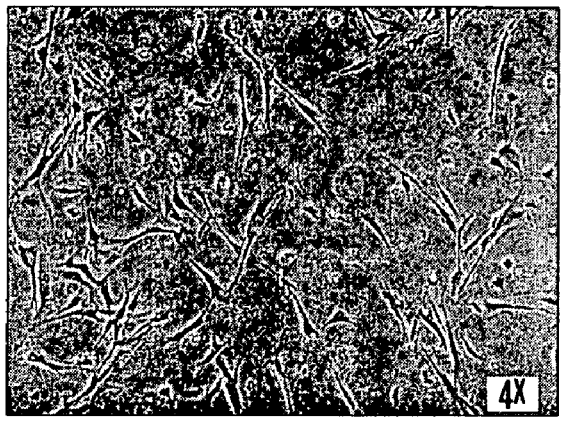
FIGS. 6A-6C shows microscopic (4×) images of a non-SACK cell strain (FIG. 6A); a SACK derived cell strain (FIG. 6B); and a SACK derived clonal cell strain (FIG. 6C).
Figure 6B:
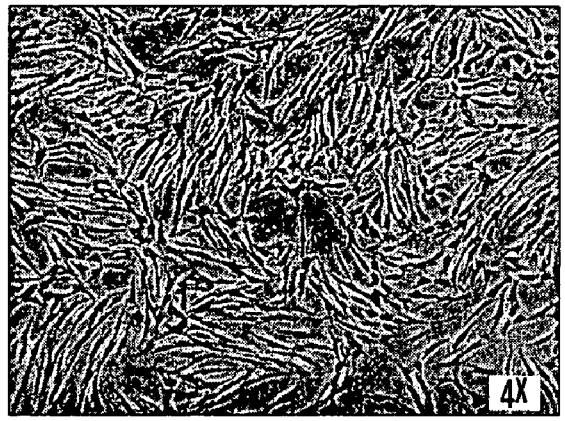
Figure 6C:
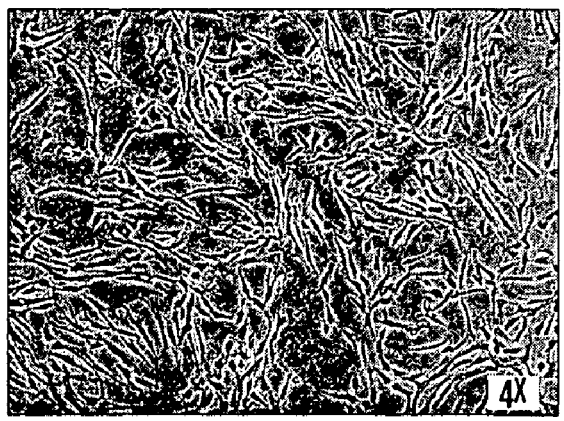

FIG. 5 shows a chart of liver cell strains that have been established using the suppression of asymmetric cell kinetics (SACK) method. Non-SACK conditions (Control) and 3 different SACK agents (HX, Xs & Xn) were used in expanding post-natal liver stem cells. 21 stable cell strains have been generated and 9 clonal sub-strains have been established. Light micrographs of various cell strains are depicted in FIG. 6.

Figure 7:
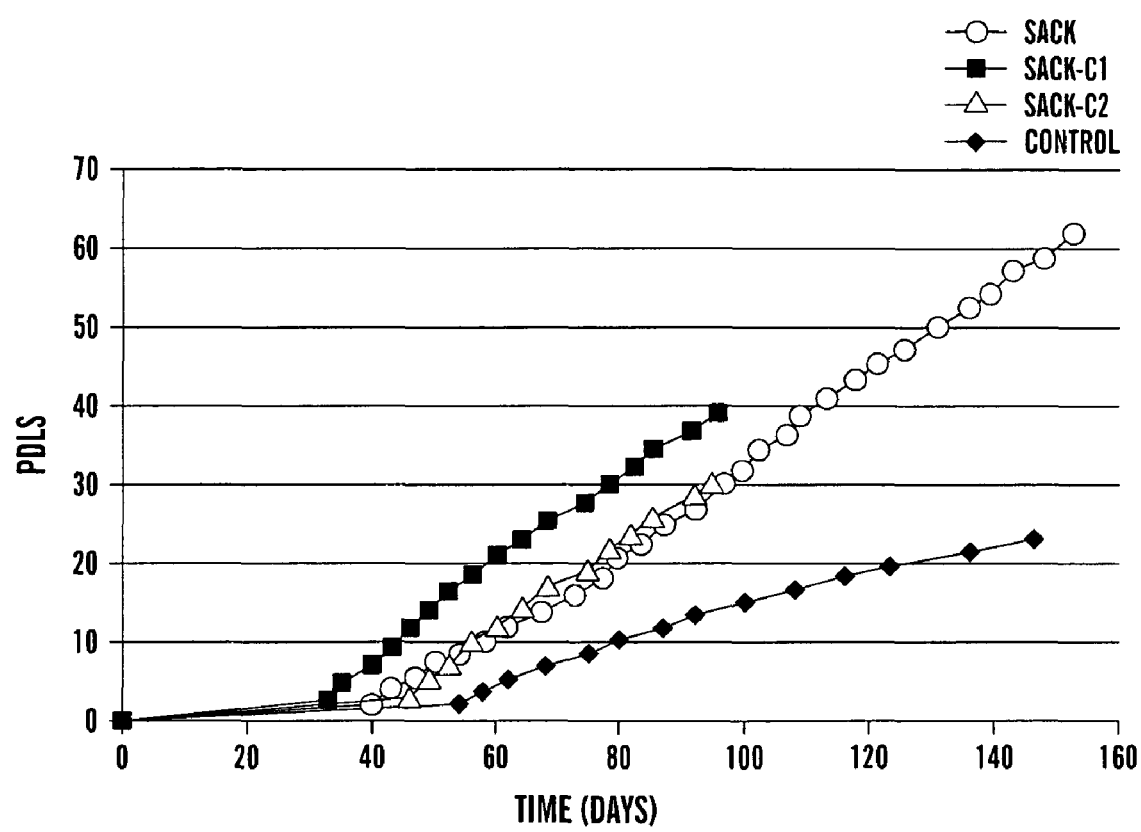
FIG. 7 shows a graph depicting population doublings (PDLs) in liver cells cultured with (SACK) or without (CONTROL) using the SACK method using 1.5 mM Xs. Compared to non-SACK culture, SACK cultures maintain a faster doubling rate. Data are also shown for two independent subclones (C1, C2) that were derived after about 21 PDLs.

As can be seen in FIG. 7, Compared to non-SACK cultures, SACK cultures maintain a faster doubling rate. Furthermore, cells cultured in SACK-supplemented medium show greater colony formation efficiency compared to SACK-free medium FIG. 8.

We evaluated several of the stable cell strains for cell kinetic properties and secretion of hepatocyte products, albumin and alpha fetal protein (AFP). Similar studies have been performed with recently derived clonal sub-strains.

Secretion Studies

Albumin and AFP are two major protein markers of the hepatocytic lineage. As hepatocytes mature, AFP expression level decreases and albumin expression increases. We evaluated SACK cultures for albumin and AFP secretion by culturing the cells under conditions that would favor differentiation of non-stem cell progeny cells. These conditions were previously established in our laboratory for the adult rat hepatic stem cell lines. Cells were grown in 10% human serum or 10% dialyzed fetal bovine serum with out any SACK agents to promote asymmetric cell kinetics and production of progeny cells. When the cell reached confluency, the medium was switched to medium supplemented with 1% serum condition for 96 hrs. After 96 hrs, the cells were washed with serum free medium and then maintained in serum free medium. Culture supernatants were sampled every 24 hrs and evaluated for albumin and AFP by western blot analysis.

Figure 11A:
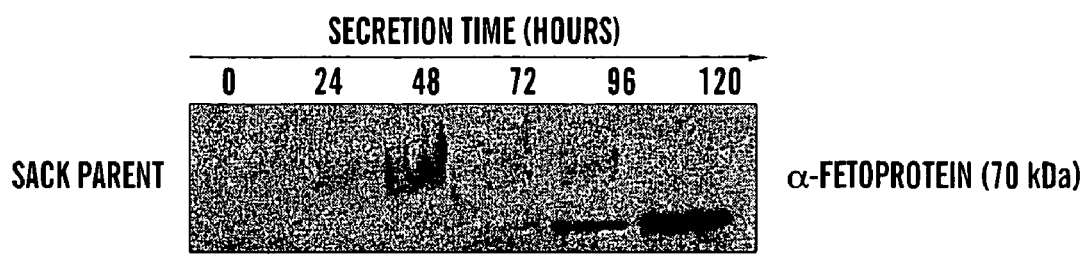
FIGS. 11A-11D show a Western Blot analysis of protein secretion in a parental SACK cell strain cultured in Human serum.
Figure 11B:
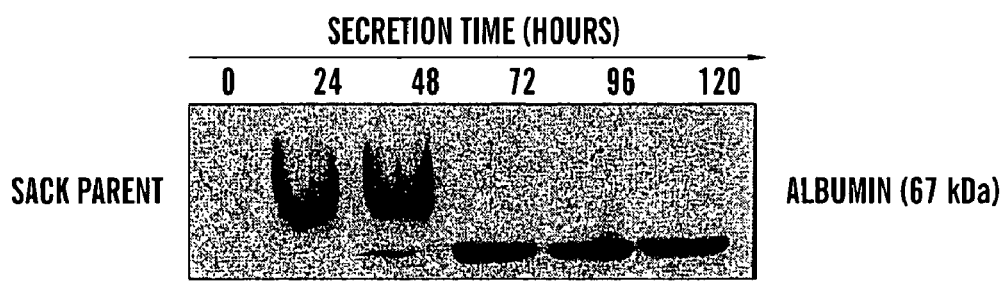
Figure 11C:
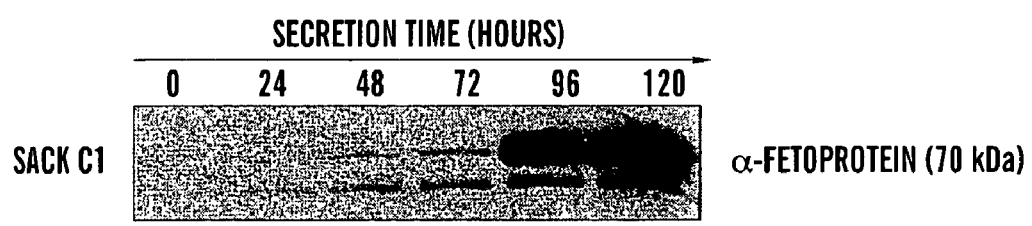
Figure 11D:
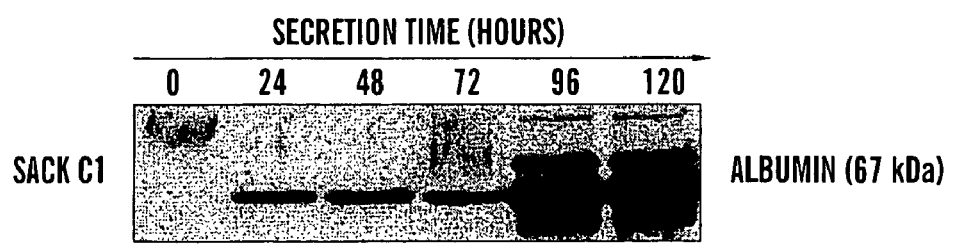

Cells cultured in dialyzed fetal bovine serum showed albumin secretion from 48 hrs. In human serum cultures, a species consistent with the modified proalbumin (MW ranges from 80-84 kDA) was observed until 48 hrs; and at 72 hrs appeared to be converted to albumin (FIG. 11B). When cells are cultured in human serum, they exhibit greatly enhanced secretion of albumin.

AFP is secreted at similar levels in medium supplemented with either dialyzed fetal bovine serum or human serum. In dialyzed fetal bovine serum, AFP secretion quickly reaches a maximum level at 24 hrs. With human serum, the accumulation kinetics were much slower and appeared to proceed through a modified pro-AFP intermediate (FIG. 11A).

Cell kinetic properties were evaluated by a colcemid arrest assay, see below.

The Colcemid Arrest Assay (CAA)

Asymmetric self-renewal is a defining property of adult stem cells. Depending on the extent of division in the non-stem cell lineage, the associated asymmetric cell kinetics can also be used to identify adult stem cells in culture. We have described the use of several assays for the detection of asymmetric cell kinetics in culture, including serial micro-colony analyses (Sherley et al., 1995ab; Lee et al., 2003), time lapse video microscopy (Rambhatla et al., 2001), and fluorescence in situ cytometry (Lee et al., 2003). We have also developed a new method for analysis of asymmetric cell kinetics in cultured cells that is based on flow cytometry detection of the production of non-cycling progeny cells. This development was motivated by our discovery that, even under differentiating conditions, adult hepatic stem cells continue to divide and produce arrested progeny which undergo cell cycle arrest coincident with differentiation (G. G. Crane and J. L. Sherley, in preparation). Therefore, we recognized that an assay that could detect the production of non-cycling cells would also be an assay for adult stem cell asymmetric self-renewal.

The new assay is called the colcemid arrest assay (CAA). We used our engineered cell lines with experimentally controlled asymmetric self-renewal to develop it (Rambhatla et al., 2001; FIG. 9). Cell cultures are treated with the microtubule antagonist colcemid for a complete generation period. Conventional methods for propidium iodine staining and standard flow cytometry are used to quantify the DNA content of cells after colcemid treatment. In the presence of colcemid, cycling cells arrest in mitosis of the cell cycle with 4N DNA content. After one generation period, all previously cycling cells contain this amount of DNA. Therefore, for cell cultures with only symmetrically cycling cells, essentially the entire culture arrests in mitosis with 4N DNA (compare FIGS. 9A and 9C). In contrast, the DNA content of non-cycling cells is unchanged. Since many types of cell cycle arrest occur in G1 phase of the cell cycle, in which the DNA content is 2N, arrested progeny cells are easily distinguished in flow cytometry from previously cycling stem cells that have been arrested by colcemid. Thus, CAA can identify and quantify the cycling stem cell fraction and the arrested differentiated progeny fraction of an asymmetrically self-renewing adult stem cell population (compare FIGS. 9B and 9D). Moreover, by performing CAA serially, it is possible to determine the rate of production of arrested progeny. In pilot studies with engineered cell lines, the CAA-determined rates were in good agreement with expectations based on previous lineage-specific cell kinetics assays.

The CAA has good sensitivity, being able to reproducibly detect arrested fractions as low as 10%. However, the specificity of the assay has two limitations. First, if progeny cells arrest in G2 of the cell cycle, which also has a 4N DNA content, they will be obscured by colcemid-arrested cycling cells. This problem is somewhat mitigated by the fact that, in general, G2 cells are a small fraction of cultured cell populations. Thus far, in independent analyses, we have not found G2 to be a significant phase for progeny cell arrest. Second, if arrested cells are produced for reasons besides asymmetric self-renewal (e.g., stochastic differentiation), the CAA cannot make this distinction. Therefore, we use the CAA as a convenient first test for asymmetric self-renewal. If CAA does not indicate production of non-cycling cells, then asymmetric self-renewal is unlikely. When they are detected, then the CAA must be supported with more specific assays like daughter pair analysis (Lee et al., 2003) to establish that adult stem cell lineages are present. Once asymmetric self-renewal is established, it is strong evidence of adult sternness; and thereafter CAA can be used for substantial high volume quantitative cell kinetics evaluations.

Cell Kinetics Evidence for Derivation of Liver Stem Cells

Figure 10A:
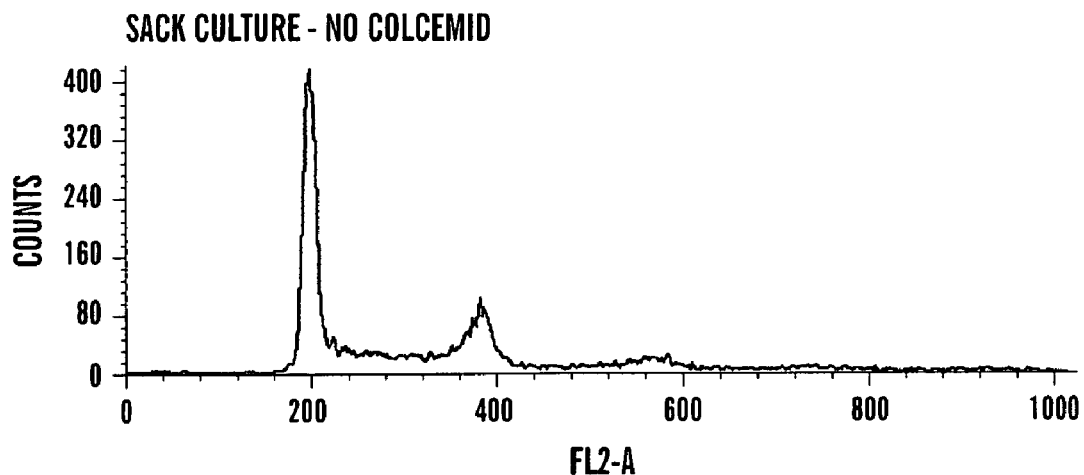
FIGS. 10A-10F shows CAA detection of non-cycling progeny cells in cycling cultures of liver stem cells.
Figure 10B:
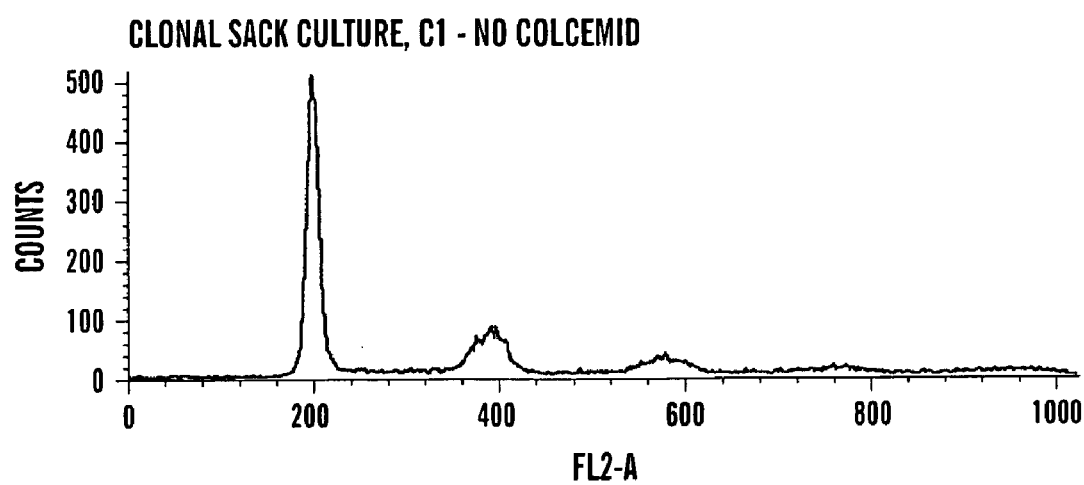
Figure 10C:
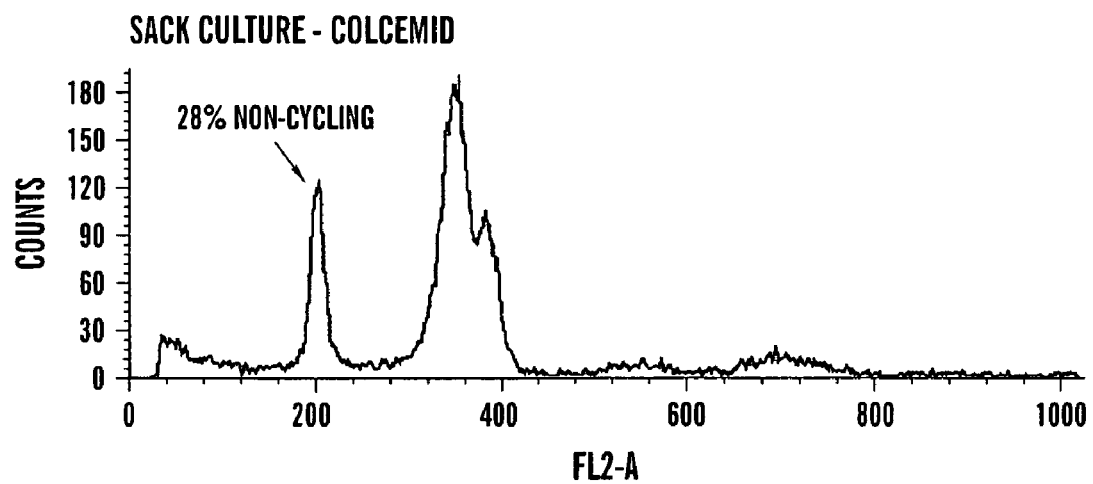
Figure 10D:
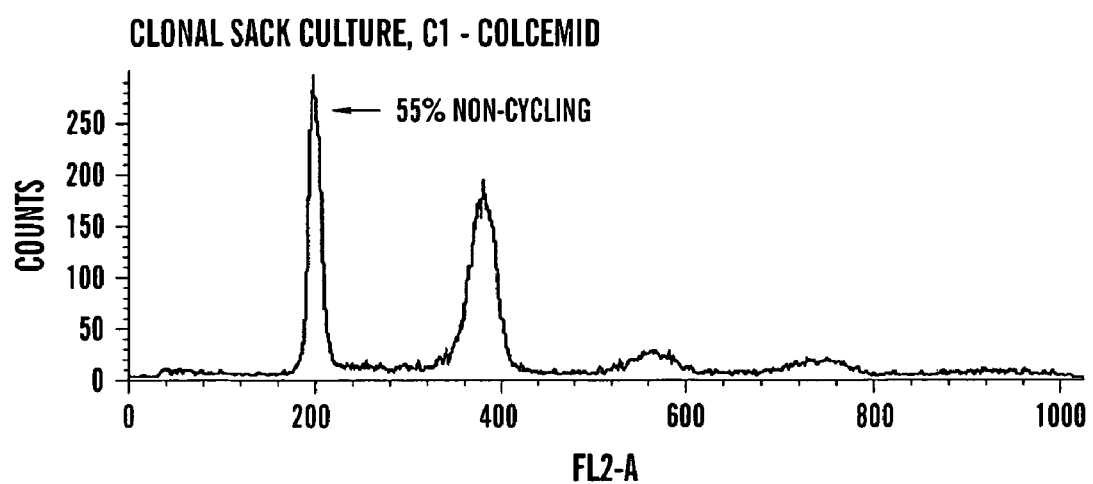
Figure 10E:
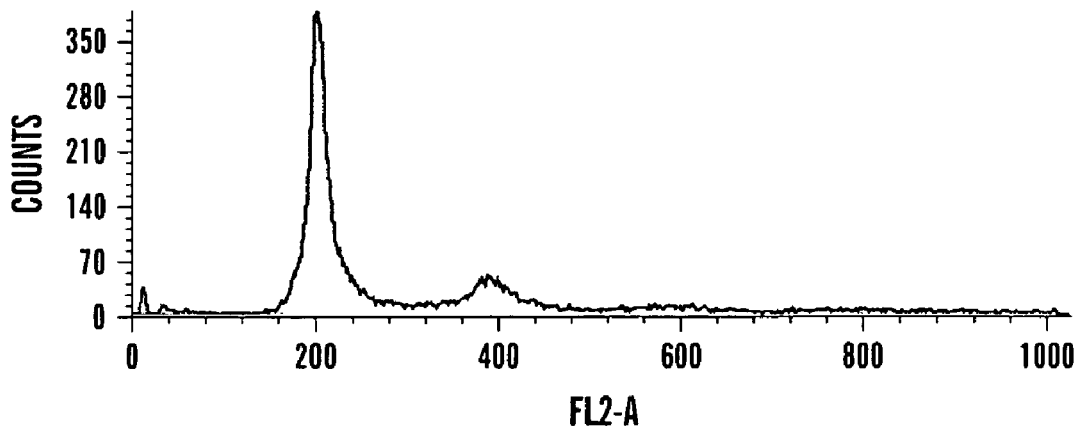
Figure 10F:
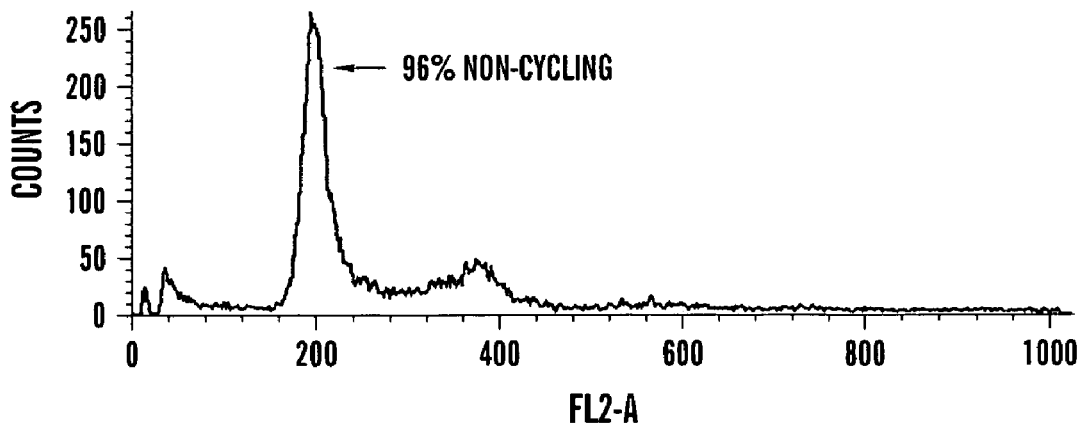

In the polyclonal SACK culture, 28% of the cells were non-cycling (FIG. 10C), compared to 96% of the non-SACK strain cells (FIG. 10E). These data indicate that both SACK and non-SACK cultures produce non-cycling cells. However, under these conditions, there is very limited proliferative capacity in the non-SACK cultures, consistent with their earlier senescence. In the clonal sub-strain, 55% of the cells were non-cycling (FIG. 10D).

The colcemid arrest assay indicates 70%-45% of the SACK lines are cycling, compared to 5% of the non-SACK. AFP and albumin are secreted by expanded cells under conditions that promote hepatocyte differentiation conditions (i.e., maintenance at confluency, at low serum concentration with EGF and TGF-beta supplementation).The cell strains show dramatically increased rates of albumin secretion when cultured medium supplemented with human serum. In addition to polyclonal SACK strains we have been able to derive clonal sub-strains with similar cell kinetics properties.

The detailed suppression of asymmetric cell kinetics (SACK) approach promotes expansion of adult human liver stem cells, while limiting the growth of their differentiating progeny. No feeder layer is required to maintain the cells in culture, and no biological matrix is required. In previous studies investigating methods of expanding post-natal human liver cells, cultures could only be maintained for a few passages. Employing the SACK method, we have been able to maintain cultures for >20 passages thus far, corresponding to approximately 43 cell doublings. We have been able to derived 21 stable cultures from 7 livers, indicating a very robust method. We have obtained a 35-fold expansion in cell number, corresponding to $7 \times 10^8$ human liver cells for each expansion. We estimate that this represents about $1 \times 10^7$ adult liver stem cells.

Example II

Derivation of Human Adult Stem Cell Strainsby SACK, Sub-clones

Although initial efforts to derive cell strains by limiting dilution cloning were unsuccessful, we modified the approach by initially culturing primary liver cell preparations at confluent cell densities under conditions of reduced serum and supplementation with SACK agents, TGF-β and EGF (See Table 1). SACK-derived rat adult stem cell strains resist hepatocytic differentiation by TGF-β and EGF. Whereas their non-stem cell progeny undergo cell cycle withdrawal and hepatic differentiation in response to serum reduction and exposure to TGF-β and EGF, in the presence of Xs, the stem cells continue to cycle actively.

Using the modified SACK method, we derived 12 independent cell lines from 2 normal livers from male donors of ages 1 and 24 years old. Although it was possible to develop strains using Hx, Xn, or Xs, so far, Xs has proven the most reliable and effective. Xs-derived cultures have been passaged as many as 120 population doublings, well past the Hayflick senescence limit of 50. In contrast, all control cell cultures, developed without SACK agent supplementation, have senesced after less than 60 population doublings. In five independent trials with multiple control cultures, four control cultures senesced after less than 30 doublings, and two did not withstand a single passage. We have also shown that the Xs-derived strains can be sub-cloned by picking single colonies after growth from platings at low cell densities.

Figure 12A:
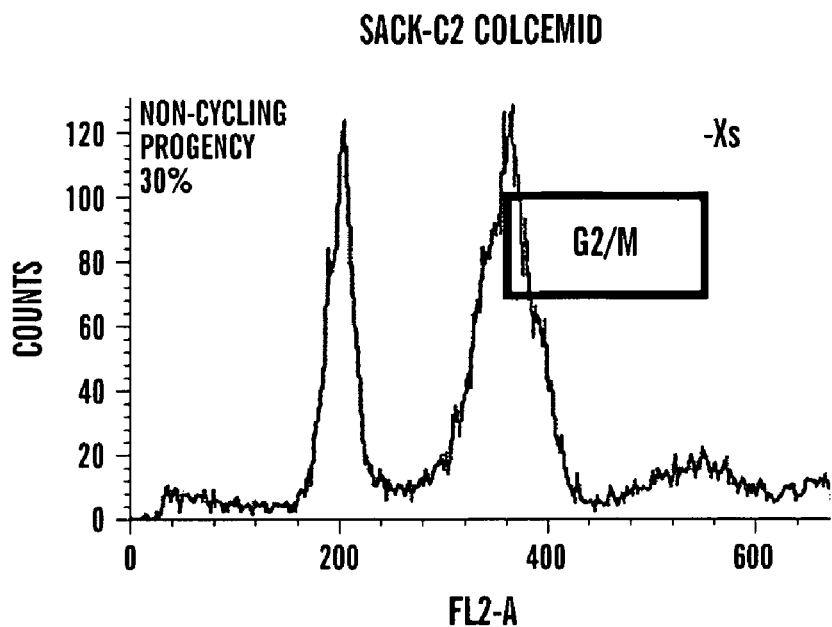
FIGS. 12A and 12B show CAA analyses of a Xs-derived sub-clone (Parental strain see FIG. 10). Subclone C2 was evaluated under conditions without (−Xs) (FIG. 12A) and with Xs supplementation (+Xs) (FIG. 12B) to demonstrate its SACK-dependency.

The Xs-derived human strains examined exhibit Xs-dependent proliferation, and analyses indicate that they possess asymmetric cell kinetics (See FIG. 12). We sometimes refer to them as putative human hepatic adult stem cell strains or adult stem cells. Hereafter, they will be referred to as "phHASCs" for simplicity.

Cells in phHASC cultures secrete α-fetoprotein, an embryonic hepatocellular marker, and secrete albumin, an indicator of mature hepatocellular differentiation (see FIG. 11). The same hepatocyte protein expression properties were noted for cultures of Xs-derived rat hepatic adult stem cell strains, which also showed inducible P450 function (Semino et al., 2003). Preliminary studies show that phHASCs express abundant PXR protein, a nuclear receptor that confers drug-inducibility to clinically important P450s like CYP3A4 (Bertilsson et al., 1998; Quattrochi and Guzelian, 2001; Willson and Kliewer et al., 2002; Burk and Wojnowski, 2004). Moreover, differentiated cultures of phHASCs show induction of CYP3A4 activity in response to two well-described inducers, the solvent dimethylsulfoxide (DMSO) and the antibiotic rifampicin (see FIG. 14).

Sub-clones Derived from SACK Method Using Xs.

We received a total of 6 cell specimens from normal human livers per our materials transfer agreement with Cambrex Biosciences (Walkersville, Md.). The specimens tested negative for human immunodeficiency virus (HIV), hepatitis B and V viruses (HBV, HCV), cytomegalovirus (CMV), and syphilis bacteria. Six liver specimens were from male donors, and one was from a female donor. All were post-natal, with ages ranging from 1 to 55 years old (median age=24 years old).

The first four livers were invested in establishing a modified SACK procedure. Unlike the original procedure developed for derivation of rat hepatic adult stem cells (Lee et al., 2003), the new method is not based on limiting dilution cloning. Instead, the liver cells are initially cultured at confluent cell densities in low serum medium (1% dialyzed fetal bovine serum [dFBS]) supplemented with the growth factors TGFβ and EGF. In addition, higher concentrations of SACK agents are used, e.g. 1.5 mM Xs. These conditions suppress the growth of differentiating liver cells (including troublesome fibroblasts and stellate cells), while promoting the expansion of phHASCs. After initial outgrowth of phHASC strains, serum supplementation is increased to 10% dFBS for routine maintenance.

Table 1 summarizes results obtained when the newly adapted SACK procedure was applied to cell specimens from two livers from 1 year-old and 24 year-old male donors. All strains were cryo-preserved at early passages using a freezing procedure that minimizes the time that cells spend super-cooled before ice formation (Karlsson et al., 1996). This precaution provides a high level of viability (70%-80%) upon thawing the cells. In addition to demonstrating successful cryo-preservation, it has been possible to efficiently sub-clone phHASC strains (Table 1).

Table 1. Summary of SACK-derived phHASC Strains

TABLE 1

| Summary of SACK-derived phHASC strains | | | |
|---|---|---|---|
| SACK agent | Number of Trials | Number of Strains | Sub-clones |
| 1 year-old male liver | | | |
| None | 2 | 0 | N/A |
| Hx | 2 | 2 | N/A |
| Xn | 2 | 1 | N/A |
| Xs | 2 | 2 | 9 |
| 24 year-old male liver | | | |
| None | 3 | 0 | N/A |
| Hx | 3 | 3 | N/A |
| Xn | 3 | 3 | N/A |
| Xs | 3 | 1 | N/A |

SACK-dependent Population Doubling Kinetics

Analysis of the cell kinetics properties of phHASC strains begins with monitoring population doubling rate during their outgrowth. As shown in FIG. 7, SACK agents like Xs preserve a high and constant population doubling rate long after control cultures undergo senescence. Control cultures have consistently undergone senescence after <60 population doublings, with a median number of 9. In contrast, Xs-derived phHASC strains have been maintained at a high doubling rates for >120 doublings. The high rate of growth is also retained in sub-clones of the initial phHASC strains (FIG. 7, SACK C1, SACK C2).

Figure 8:
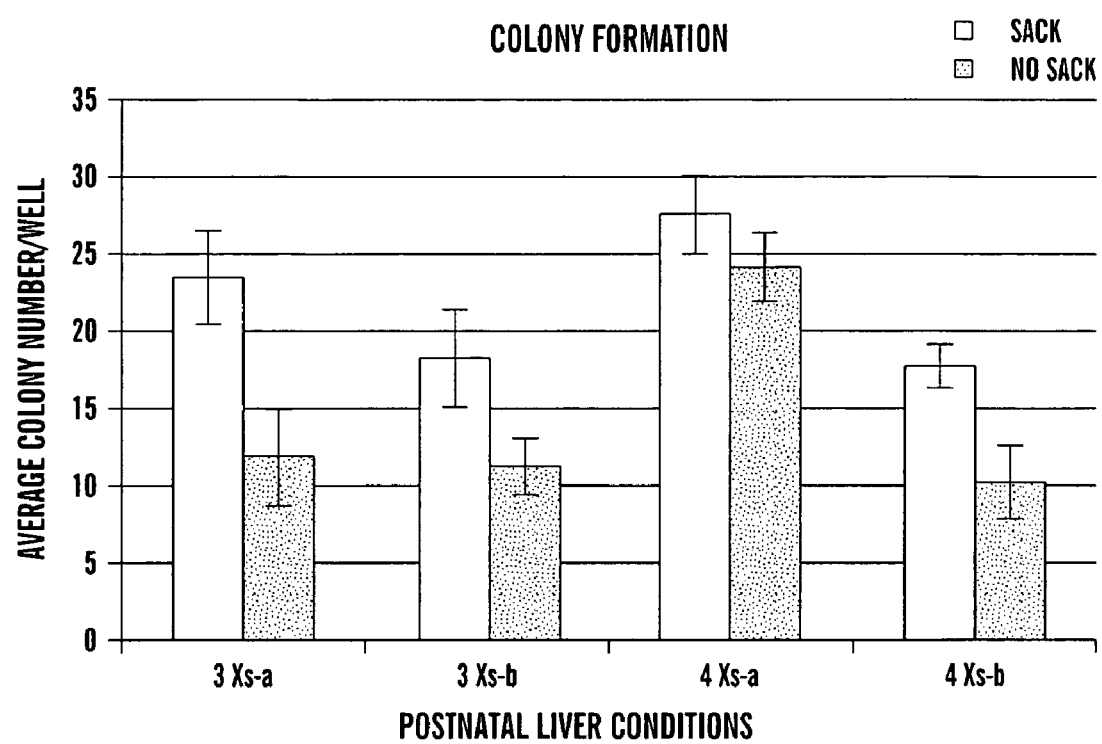
FIG. 8 shows that cells cultured in SACK-supplemented medium show greater colony formation efficiency compared to SACK-free medium. A colony formation study was performed to evaluate the effects of SACK agents on 4 different SACK cultures (FIG. 5 Liver 3, Xs-a, Xs-b; Liver 4 Xs-a, Xs-c). Bar heights indicate the mean number of colonies formed after plating 300 cells per well in 6 well plates (n=6) either in SACK or no-SACK condition. 24 hrs later media was changed again. Cells were grown for 2 weeks and then stained with crystal violet stain. Error bars indicate the standard deviation of the 6 replicate cultures.
Figure 9A:
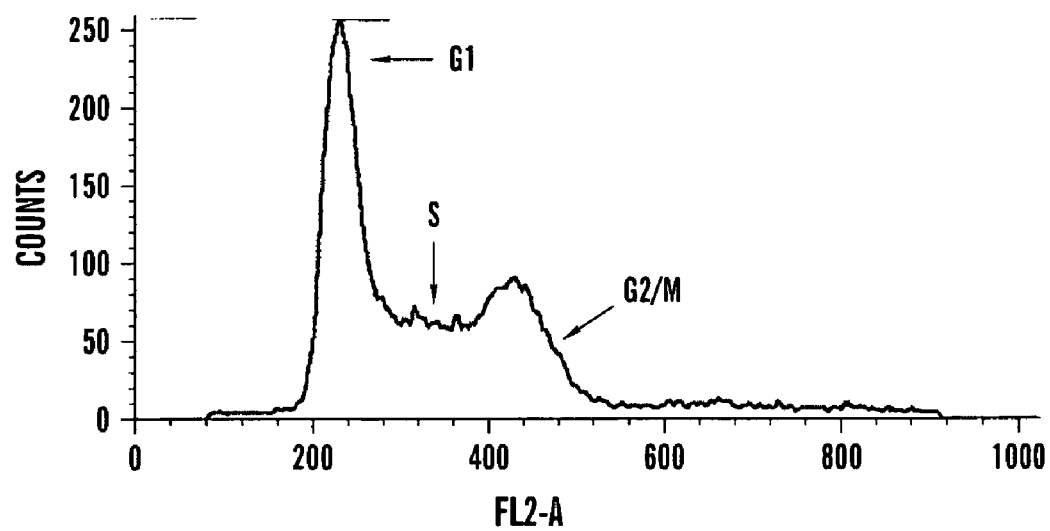
FIGS. 9A-9D show that a colcemid arrest assay (CAA) can detect asymmetric self-renewal in cultures of engineered cell lines. After 24 hours of culture, p53-null cells (FIGS. 9A and 9C) and p53-expressing cells (FIGS. 9B and 9D) grown under conditions that induce asymmetric self-renewal in cultures of p53-inducible cells, were either allowed to continue growth (FIG. 9A and FIG. 9B) or were treated with colcemid (FIG. 9C and FIG. 9D). Shown are flow cytometry histograms from analyses of untreated and treated cultures for propidium iodine fluorescence, indicating relative DNA content.
Figure 9B:
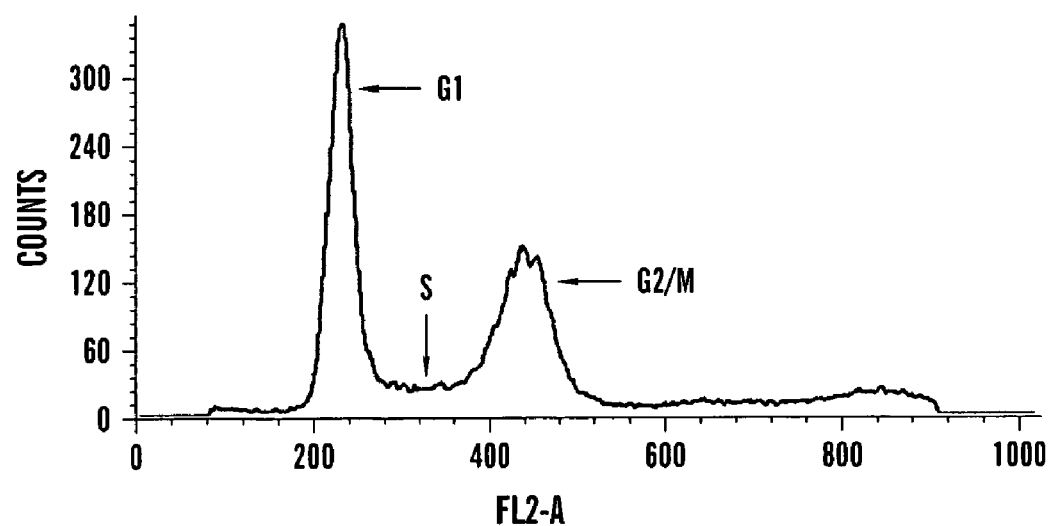
Figure 9C:
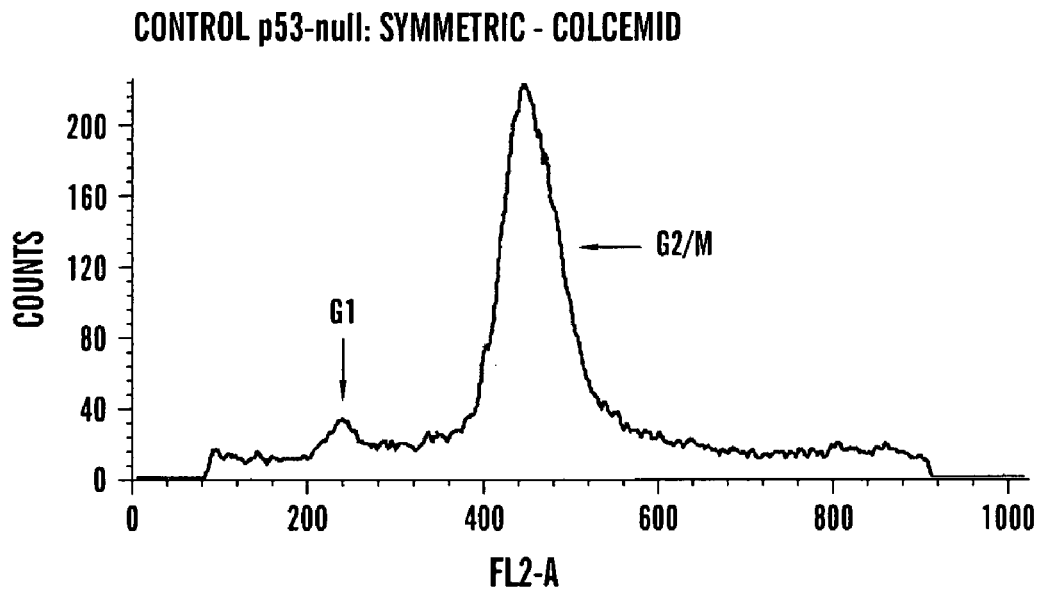
Figure 9D:
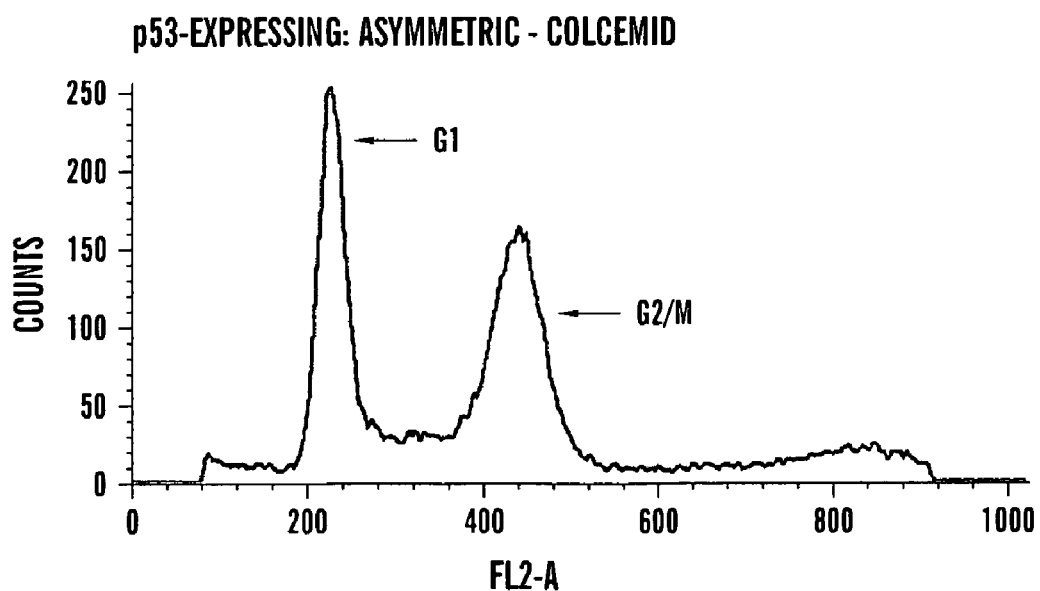

Consistent with SACK agents being responsible for the outgrowth of phHASC strains, they are SACK agent-dependent for growth. As shown in FIG. 8, SACK-derived hepatic cell strains show significantly reduced ability to form colonies when the SACK agent is withdrawn. The SACK agent-dependency in colony formation analyses was also observed for clonal phHASC strains.

SACK-dependent Asymmetric Cell Kinetics

Two related assays were performed to evaluate the cell kinetics symmetry of cells in phHASC cultures. The first was an in situ cytometry assay described previously for evaluation of the cell kinetics symmetry of SACK-derived rat hepatic adult stem cell strains (Lee et al., 2003). The assay is called a "daughter pair analysis" (DPA). It is based on the observation that arrested daughters of asymmetric cell kinetics divisions in vitro often do not enter S phase and replicate their DNA (Sherley et al., 1995a; Lee et al., 2003). To perform DPA, cells were plated at micro-colony density (~400 cells per cm$^2$). After allowing about 24 hours for cell division to produce "daughter pairs", the cells were cultured for 24 hours with the thymidine analogue bromodeoxyuridine (BrdU). The cells were then fixed and evaluated for BrdU incorporation by in situ immunofluorescence with anti-BrdU antibodies using fluorescence imaging and scanning laser cytometry.

Because daughters of symmetrically cycling cells proceed through the cell cycle with a high degree of synchrony, if one daughter incorporates BrdU, the other does, too. This relationship yields symmetric daughter pairs in which both cells are positive for BrdU uptake. Nearly 80% of BrdU-positive daughter pairs in initial phHASC cultures were of this type. The remaining approximately 20% were asymmetric, with one positive and one negative cell in the pair. BrdU identifies the cycling daughter that has entered or traversed S phase, unlike its unlabeled sister that undergoes a post-mitotic arrest. The asymmetric daughter pairs were not simply due to statistical asynchrony between two cycling daughters. The 24-hour labeling period insured sufficient time for cycling cells to enter or traverse S phase during the labeling period. Therefore, the asymmetric daughter pairs are indicative of cells that cycle asymmetrically to produce another cycling cell (i.e., putative adult stem cells) and an asymmetric daughter that undergoes cell cycle arrest. This feature was shown to be a gnomonic for adult stem cells in cultures of SACK-derived rat adult hepatic stem cells (Lee et al., 2003; Semino et al., 2003).

The DPA is ideal for discrete detection of cells undergoing asymmetric cell kinetics. It can be used as a quantitative tool as well (Lee et al., 2003). However, it is not ideally suited for rapid examination of multiple cell strains for asymmetric cell kinetics. For the purpose of evaluating the SACK-dependency of asymmetric cell kinetics detected in multiple phHASC strains, we developed a second method that provides higher throughput. The second assay is called the colcemid arrest assay (CAA) and is described in Example 1.

Figure 12B:
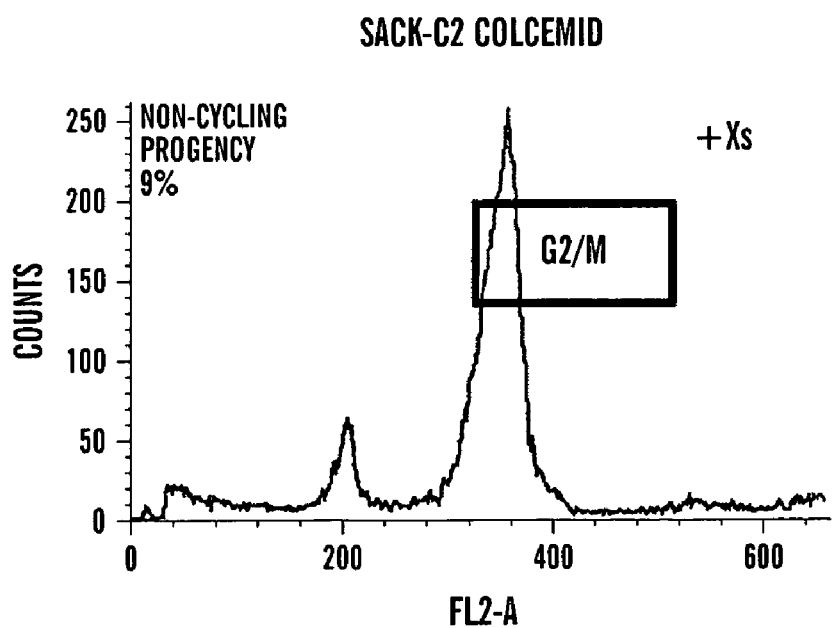

Both phHASC strains and their sub-clones display a significant fraction of non-cycling cells in the CAA (FIG. 10, SACK-Parent and SACK-C1). Moreover, the non-cycling fraction can be reduced when SACK agents are added to the medium (FIG. 12, Colcemid SACK-C2; compare –Xs (FIG. 12A) to +Xs (FIG. 12B). These data are strong evidence that phHASC cell strains originate from asymmetrically cycling cells in human livers and can be considered adult stem cells. Based on previous studies with SACK-derived rat adult hepatic stem cell strains, this property is highly predictive of adult stem cell function.

Secretion of Hepatocyte-specific Proteins

As a first test of whether phHASCs were of hepatocyte lineage and produced progeny cells with mature hepatocyte functions, we investigated the ability of cells to express and secrete α-fetoprotein and albumin. Expression of α-fetoprotein is indicative of relatively undifferentiated hepatic cells (hepatocytic or biliary epithelial); and secretion of albumin is a mature hepatocyte function. To induce differentiation of progeny cells, cultures were grown to confluence in Xs-free medium and then maintained for several days in medium supplemented with 1% dFBS (instead of the 10% level used for maintenance), TGF-β and EGF. This procedure induces hepatic differentiation by non-stem cell progeny cells in cultures of Xs-derived rat hepatic adult stem cells. As shown in FIG. 11, both parental phHASC strains and sub-cloned strains produce cells that secrete α-fetoprotein and albumin, consistent with the expectation that both primitive and mature cells are present in these cultures. Secretion remains robust in cultures and subclones that have been maintained in culture for >120 population doublings.

We noted that at early times during secretion analyses, high molecular weight protein forms were detected in the immunoblots (see FIG. 11). These may be previously unrecognized oligosacharride-modified forms of the proteins.

Example III

Expression of Inducible Cytochrome P450 Activity

We have demonstrated two important properties of adult stem cells 1) expression of the PXR nuclear receptor that mediates the induction response of cytochrome P450 CYP3A4 to drugs and xenobiotics; and 2) expression of inducible CYP3A4 activity. The demonstration of these properties validates our SACK approach for developing stable cell strains with these highly desired properties for drug discovery research and pre-clinical evaluations of drug toxicology and drug interactions. Derivatives of SACK derived cell strains that express inducible CYP3A4 can be made that stably express CYP3A4 promoter-GFP, -CFP, YFP fluorescent protein gene constructs, for use in high throughput assays.

The expression of the 44 kDa molecular weight PXR nuclear receptor by a phHASC parent strain and two expanded subclones was evaluated in immunoblot analyses with anti-PXR antibodies. Two different sources of antibodies were used with similar results. One antibody was an affinity-purified, polyclonal IgG fraction from a rabbit anti-PXR antiserum (Abcam, Cambridge, Mass.); and the other was a polyclonal antibody affinity-purified from goat antisera raised against an N-terminal peptide of PXR (Santa Cruz Biotechnology, Santa Cruz, Calif.). Both the parent strain and its subcloned derivatives expressed a significant level of PXR protein, comparable to the level detected in HepG2 human hepatoma cells.

Figure 13:
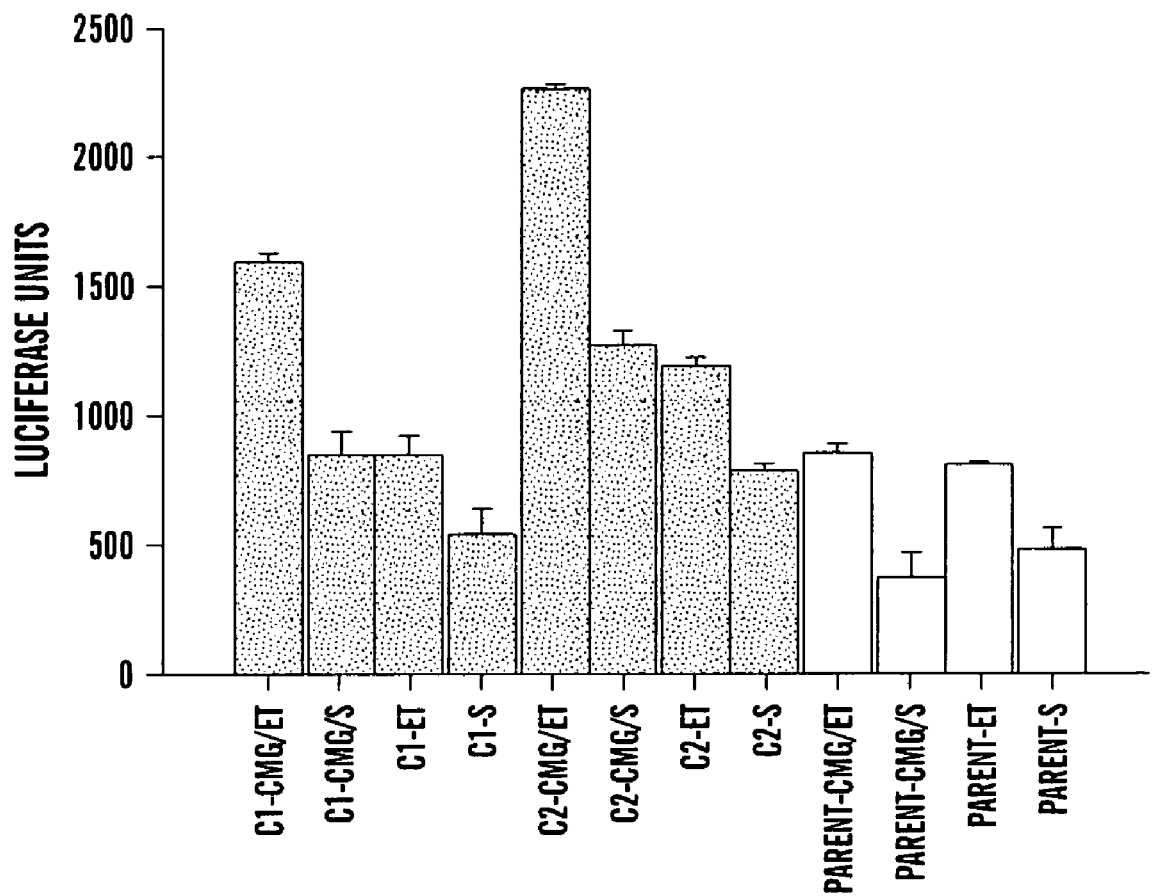
FIG. 13 shows a graph depicting detection of CYP3A4 activity in phHASC strains. The p450-GLO™ CYP3A4 luminescent assay was used to assay a parental phHASC strain (Parent) and two of its clonal derivatives (C1, C2) for CYP3A4 activity. Intact cells were assayed in situ after growth under four different conditions: S, routine culture conditions with serum supplementation; ET, routine culture conditions with serum-free medium supplemented with EGF/TGF-β1; CMG/S, Collagen-Matrigel™ sandwich with serum supplementation; and CMG/ET, Collagen-Matrigel™ sandwich with serum-free medium supplemented with EGF/TGF-β1. Data are the mean of replicate assays (n=2). Error bars indicate the standard deviation of replicate assays.

We undertook an evaluation of CYP3A4 activity in phHASC strains using a commercially available luciferase-based luminescent assay. The p450-GLO™ CYP3A4 luminescent assay was supplied by Promega Corp. (Madison, Wis.). The assay is based on a caged luciferin substrate that is specifically uncaged by the enzymatic action of CYP3A4. Once uncaged, luciferin is available for luciferase action and light production. As shown in FIG. 13, both a Xs-derived parental phHASC strain and two of its clonal derivatives (C1 and C2) exhibit significant levels of CYP3A4 enzymatic activity. The clonal strains consistently exhibit a higher level of activity than the parent under several different conditions of growth.

Intact cells were assayed after culture under the following conditions to evaluate effects of differentiating agents: on standard tissue culture plastic with medium supplemented with serum or supplemented with combined epidermal growth factor (EGF) and transforming growth factor-β1 (TGF-β1); or sandwiched between collagen and Matrigel™ with medium supplemented with either serum or EGF and TGF-β1. The SACK agent xanthosine (Xs) was removed in all cases to promote asymmetric self-renewal of hepatic ASCs and production of differentiating progeny cells. The collagen-Matrigel™ sandwich condition is recommended by the supplier for the assay of primary hepatocytes. Collagen-Matrigel™ sandwiching and EGF/TGF-β1 supplementation under serum-free conditions maintain and induce hepatocyte differentiation, respectively. Consistent with increased hepatocytic differentiation, all three evaluated phHASC strains exhibited increased CYP3A4 activity when cultured in serum-free medium with EGF/TGF-β1 supplementation (FIG. 13).

Plating in collagen-Matrigel™ was only associated with increased CYP3A4 activity for the clonal cell strains (FIG. 13, C1 and C2, CMG). It is unlikely that the observed differences in CYP3A4 activity are due to differences in cell number, as all cell cultures were confluent at the time of assay. They may reflect differences in the proportions of stem cells and their differentiated progeny cells in cultures or differences in their respective responses to extracellular matrix factors. These properties indicate that phHASCs can be used for study of P450 activity regulation.

Figure 14A:
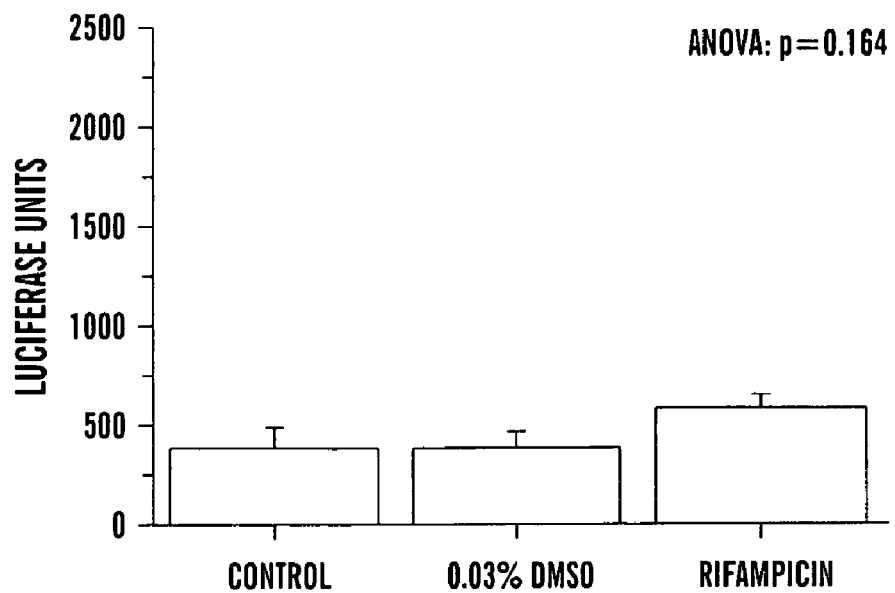
FIGS. 14A and 14B show graphs depicting induction of CYP3A4 activity in a parental phHASC strain after exposure to rifampicin. Intact cells of a Xs-derived, parental phHASC strain were assayed for CYP3A4 activity after culture for 48 hours in Xs-free medium, Xs-free medium supplemented with either 0.03% or 5% DMSO, or Xs-free medium supplemented with the respective DMSO concentration and 10 μM rifampicin.
Figure 14B:
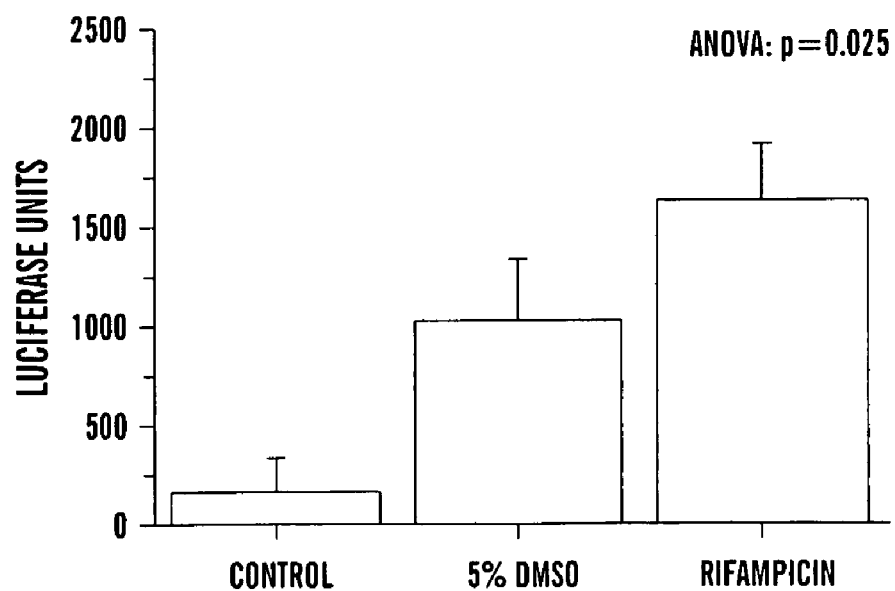

As an evaluation of the drug-inducibility of CYP3A4 in phHASC strains, we treated a well-characterized, Xs-derived, parental strain with the antibiotic rifampicin and assayed for CYP3A4 activity using the p450-GLO™ CYP3A4 luminescent assay (FIG. 14). We evaluated the effect of rifampicin under two different conditions with two different concentrations of the solvent carrier DMSO, 0.03% and 5%. Parental phHASCs were evaluated after growth in a collagen-Matrigel™ sandwich, as recommended by the supplier of the p450-GLO™ CYP3A4 luminescent assay (FIG. 14A) or under standard culture conditions with serum-free medium (FIG. 14B). At high concentrations ($\geq 1\%$), DMSO is a known inducer of CYP3A4 activity in primary human hepatocytes (Raucy et al., 2002). At the 5% concentration under serum-free conditions, DMSO induced a 6.5-fold increase in CYP3A4 activity (FIG. 14B). In contrast, at the lower concentration with cells grown in a collagen-Matrigel™ sandwich, DMSO did not affect the basal level of CYP3A4 activity.

Under both conditions, addition of 10 μM rifampicin (48 hour exposure) was associated with a 1.5-fold increase in CYP3A4 activity above the level in cells exposed to DMSO alone. In previous studies, this concentration of rifampicin was shown to be optimal for CYP3A4 induction in primary human hepatocytes (Raucy et al., 2002; Raucy, 2003; Yeuh et al., 2005). Moreover, a recent study using the same p450-GLO™ CYP3A4 luminescent assay reported a 1.6-fold to 1.7-fold induction of CYP3A4 activity in primary human hepatocytes exposed to 10 μM rifampicin for 36 and 60 hours, respectively (Yeuh et al., 2005).

Gene Expression Profiling of phHASC Cells Strains for Liver Specific Gene Expression To supplement characterizations based on a few selected hepatocyte-specific secreted proteins and P450 enzyme assays, we performed preliminary analyses of the global mRNA expression profile of phHASC strains with a focus on well-defined human liver-specific genes. Gene microarray analyses were performed in triplicate for phHASC subclones C1 and C2 grown under routine culture conditions with Xs-supplementation. As a comparison standard, gene micro-array analyses were performed in duplicate with a typical starting preparation of normal donor human liver cells. CodeLink UniSet Human 20K Bioarray General Electric Healthcare (GEH) microarrays were used. These studies were conducted in collaboration with Dr. Roderick Jensen in the Biotechnology Center of the University of Massachusetts-Boston.

Out of 71 human liver-specific genes represented on GEH microarrays (From ~300 genes listed in the Cold Spring Harbor Laboratory Liver-Specific Promoter Database (LSPD); the expression of 59 (83%) was detected in the starting liver cell preparation. Of these, expression of 15 (25%) was detected in both C1 and C2 cells. These genes are listed in Table 2. It is noteworthy that genes like α-fetoprotein, albumin, and CYP3A4 were not detected. However, the microarray analyses were not performed with cells under conditions that induce hepatocyte differentiation. Therefore, mature hepatocyte genes were predicted to be under-represented among genes expressed in the clonal phHASC strains in this initial microarray evaluation.

TABLE 2

Human liver-specific gene expression detected in clonal phHASC strains undergoing active cell proliferation.

I. High Expression in Liver Cells and Clonal phHASC Strains 1. enolase 1, (alpha) (ENO1)

II. Higher Expression in Liver Cells (3-fold to >1000-fold)

2. fibrinogen, B beta polypeptide (FGB)
3. coagulation factor IX (plasma thromboplastic component, Christmas disease, hemophilia B) (F9)
4. argininosuccinate synthetase (ASS), transcript variant 2
5. epoxide hydrolase 1, microsomal (xenobiotic) (EPHX1)
6. lecithin-cholesterol acyltransferase (LCAT)
7. cAMP responsive element binding protein 1 (CREB1), transcript variant B
8. *Hsapiens* HNF1-C mRNA III. Higher Expression in Clonal phHASC Strains (2-fold to 16-fold)

9. alcohol dehydrogenase 5 (class III), chi polypeptide (ADH5)
10. carcinoembryonic antigen-related cell adhesion molecule 5 (CEACAM5)
11. Similar to gb: D00096 TRANSTHYRETIN PRECURSOR (HUMAN);
12. HNC18-1-D8R HNC (Human Normal Cartilage) *Homo sapiens* cDNA
13. 3-hydroxy-3-methylglutaryl-Coenzyme A reductase (HMGCR)
14. plasminogen activator, tissue (PLAT), transcript variant 3
15. gamma-glutamyl hydrolase (conjugase, folylpolygammaglutamyl hydrolase) (GGH)

The expression levels of liver-specific genes detected in the two independently derived subclones were highly correlated ($R^2=1.00$; $p<0.0001$). However, the gene expression levels of clones were not correlated with expression levels of primary liver cells. In Table 2, genes are grouped into three expression categories. Only one gene, enolase I, showed similar high level expression in both clonal phHASCs strains and primary liver cells. The other genes showed higher expression in either clonal phHASCs strains or primary liver cells. Though not performed under conditions that promote ideal hepatocyte differentiation, these initial studies support that clonal phHASC cells are of hepatic lineage.

REFERENCES

Anzenbacher, P., and Anzenbacherová E. (2001) Cytochromes P450 and metabolism of xenobiotics. Cell Mol Life Sci. 58, 737-747.

Berardi, A. C., Wang, A., Levine, J. D., Lopez, P., Scadden, D. T. (1995) Functional isolation and characterization of human hematopoetic stem cells. *Science* 267, 104-108.

Bernstein, A., Dick, J. E., Huszar, D., Robson, I., Rossant, J., Magli, C., Estrov, Z., Freeman, M., and Phillips, R. A. (1986) Genetic engineering of mouse and human stem cells. *Cold Spring Harbor Symposia on Quantitative Biology* LI, 1083-1091.

Bertilsson, G., Heidrich, J., Svensson, K., Asman, M., Jendeberg, L., Sydow-Backman, M., Ohlsson, R., Postlind, H., Blomquist, P., and Berkenstam, A. (1998) Identification of a human nuclear receptor defines a new signaling pathway for CYP3A induction. Proc Natl Acad Sci USA. 95, 12208-12213.

Burk, O. and Wojnowski, L. (2004) Cytochrome p450 3A and their regulation. Arch. Pharmacol. 369, 105-124.

Brenner, M. K. (1996). Gene transfer to hematopoetic cells. *New Engl. J. Med.* 335, 337-339.

Cairns, J. (1975). Mutation selection and the natural history of cancer. *Nature* 255, 197-200.

Cheshier, S. H., Morrison, S. J., Liao, X. and Weissman, I. L. (1999) In vivo proliferation and cell cycle kinetics of long-term self-renewing hematopoetic stem cells. *Proc. Natl. Acad. Sci. USA* 96, 3120-3125.

Collart, F. R., Chubb, C. B., Mirkin, B. L., and Huberman, E. (1992) Increased inosine-5'-phosphate dehydrogenase gene expression in solid tumor tissues and tumor cell lines. *Cancer Res.* 52, 5826-5828.

Dearden, P. and Akam, M. (2000) Segmentation in silico. *Nature* 406, 131-132.

Donato, M. T., Jiménez, N., Castell, J. V., and Gómez-Lechón, M. J. (2004) Fluorescence-based assays for screening nine cytochrome P450 (P450) activities in intact cells expressing individual human P450 enzymes. Drug Metab Dispos. 32, 699-706.

El-Deiry, W. S., Tokino, T., Velculescu, V. E., Levy, D. B., Parsons, R., Trent, J. M., Lin, D., Mercer, W. E., Kinzler, K. W., and Vogelstein, B. (1993) WAF1, a potential mediator of p53 tumor suppression. *Cell* 75, 817-825.

Epperly, M. W., Bray, J. A., Carlos, T. M., Prochownik, E., and Greenberger, J. S. (1999) Biology of marrow stromal cell lines derived from long-term bone marrow cultures of Trp53-deficient mice. *Radiation Res.* 152, 29-40.

Fuchs, E. and Segre, J. A. (2000) Stem cells: A new lease on life. *Cell* 100, 143-155.

Gardner-Stephen, D., Heydel, J. M., Goyal, A., Lu, Y., Xie, W., Lindblom, T., Mackenzie, P., and Radominska-Pandya, A. (2004) Human PXR variants and their differential effects on the regulation of human UDP-glucuronosyl-transferase gene expression. Drug Metab Dispos. 32, 340-347.

Giaccia, A. J. and Kastan, M. B. (1998) The complexity of p53 modulation: emerging patterns from divergent signals. *Genes & Dev.* 12, 2973-2983.

Gibson-D'Ambrosio, R. E., Crowe, D. L., Shuler, C. E., and D'Ambrosio, S. M. (1993) "The Establishment and Continuous Subculturing of Normal Human Adult hepatocytes: Expression of Differentiated Liver Functions", Cell Biology and toxicology, 9, 385-403.

Goodell, M. A., Brose, K., Paradis, G., Conner, A. S., and Mulligan, R. C. (1996) "Isolation and functional properties of murine hematopoetic stem cells that are replicating in vivo." *J. Exp. Med.* 183, 1797-1806.

Goodell, M. A., Rosenzweig, M., Kim, H., Marks, D. F., DeMaria, M., Paradis, G., Grupp, S. A., Sieff, C. A., Mulligan, R. C. and Johnson, R. P. (1997) Dye efflux studies suggest that hematopoetic stem cells expressin low or undetectable levels of CD34 antigen exist in multiple species. *Nature Med.* 3, 1337-1345.

Goodwin, B., Hodgson, E., and Liddle, C. (1999) The orphan human pregnane X receptor mediates the transcriptional activation of CYP3A4 by rifampicin through a distal enhancer module. Mol Pharmacol. 56, 1329-1339.

Grisham, J. W. and Thorgeirsson, S. S. (1997) Liver stem cells. In Stem Cells, C. S. Potten, ed. (San Diego, Calif.: Harcourt Brace & Co.), pp. 1-28.

Gottleib, T. M. and Oren, M. (1996) p53 in growth control and neoplasia. *Biochim. Biophys. Acta* 1287, 77-102.

Greenberger, J. S., Epperly, M. W., Zeevi, A., Brunson, K. W., Goltry, K. L., Pogue-Geile, K. L., Bray, J. and Berry, L. (1996) Stromal cell involvement in leukemogenesis and carcinogenesis. in vivo 10, 1-18.

Gridelli, B. and Remuzzi, G. (2000) Strategies for making more organs available for transplantation. New Engl. J. Med. 343, 404-410.

Grisham, J. W. and Thorgeirsson, S. S. (1997) Liver stem cells. In Stem Cells, C. S. Potten, ed. (San Diego, Calif.: Harcourt Brace & Co.), pp. 1-28.

Gu, J. J., Stegmann, S., Gathy, K., Murray, R., Laliberte, J., Ayscue, L., and Mitchell, B. S. (2000) Inhibition of T lymphocyte activation in mice heterozygous for loss of the IMPDH gene. *J. Clin. Invest.* 106, 599-606.

Hauschka, P. V. (1973) "Analysis of nucleotide pools in animal cells" in *Methods in Cell Biology*, Prescott, D. M., ed. Academic Press (New York) Vol. VII, pp. 361-462.

Heim, R., Prasher, D., Tsien, R. (1994) Wavelength mutations and posttranslational autoxidation of green fluorescent protein. Proc. Natl. Acad. Sci. USA. 91, 12501-12504.

Herrero-Jimenez, P., Thilly, G., Southam, P. J., Tomita-Mitchell, A., Morgenthaler, S., Furth, E. E., and Thilly, W. G. (1998). Mutation, cell kinetics, and subpopulations at risk for colon cancer in the United States. *Mutation Res.* 400, 553-578.

Hollstein, M., Sidransky, D., Vogelstein, B., and Harris, C. C. (1991) p53 mutations in human cancers. *Science* 253, 49-53.

Huang, S., Law, P., Francis, K., Palsson, B. O., and Ho, A. D. (1999) "Symmetry of initial cell divisions among primitive hematopoetic progenitors is independent of ontogenic age and regulatory molecules." *Blood* 94, 2595-2604.

Jackson, R. C., Weber, G., and Morris, H. P. (1975) IMP dehydrogenase, an enzyme linked with proliferation and malignancy. *Nature* 256, 331-333.

Jardim, A., Bergeson, S. E., Shih, S., Carter, N., Lucas, R. W., Merlin, G., Myler, P. J., Stuart, K., and Ullman, B. (1999) Xanthine phosphoribosyltransferase from *Leishmani donovani*. Molecular cloning, biochemical characterization, and genetic analysis. *J. Biol. Chem.* 274, 34403-34410.

Jones, S. A., Moore, L. B., Shenk, J. L., Wisely, G. B., Hamilton, G. A., McKee, D. D., Tomkinson, N.C., LeCluvse, E. L., Lambert, M. H., Willson, T. M., Kliewer, S. A., and Moore, J. T. (2000) The pregnane X receptor: a promiscuous xenobiotic receptor that has diverged during evolution. Mol Endocrinol. 14, 27-39.

Jordan, C. T. and Lemischka, I. R. (1990) Clonal and systemic analysis of long-term hematopoiesis in the mouse. *Genes Dev.* 4, 220-232.

Knudson, A. G. (1992) Stem cell regulation, tissue ontogeny, and oncogenic events. *Seminars in Can. Biol.* 3, 99-106.

Kobayashi, K., Rochat, A., and Barrandon, Y. (1993) Segregation of keratinocyte colony-forming cells in the bulge of the rat vibrissa. *Proc. Natl. Acad. Sci.* USA 90, 7391-7395.

Kornberg, A. (1980) *DNA replication*, ed. 2. W. H. Freeman and Co., San Francisco, Calif.

Latham, K. M., S. W. Eastman, A. Wong, and P. W. Hinds. (1996). Inhibition of p53-mediated growth arrest by overexpression of cyclin-dependent kinases. *Mol. Cell. Biol.* 16, 4445-4455.

Latt, S. A., George, Y. S., and Gray, J. W. (1977) Flow cytometric analysis of bromodeoxyuridine-substituted cells stained with 33258 Hoechst *J. Histochem. Cytochem.* 25, 927-934.

Lee, H.-S., Crane, G. G., Merok, J. R., Tunstead, J. R., Hatch, N. L., Panchalingam, K., Powers, M. J., Griffith, L. G., and Sherley, J. L. (2003) "Clonal Expansion of Adult Rat Hepatic Stem Cell Lines by Suppression of Asymmetric Cell Kinetics (SACK)", *Biotech. & Bioeng.* 83, 760-771.

Lee, H.-S., Sherley, J. L., Chiou, L.-L., Chen, J. J. W., Lai, H.-S., Chiu, C.-C., Chen, C.-H., Huang, G.-T., Sheu, J.-C., and Yang, P.-C. (2004) "Differential Expression of Neogenin and Epithelial Membrane Protein-1 in an Adult Rat Liver Stem Cell Line," submitted.

Leong, P.-M., Thilly, W. G., and Morgenthaler, S. (1985) Variance estimation in single-cell mutation assays: comparison to experimental observations in human lymphoblasts at 4 gene loci.

Levine, A. J. and Momand, J. (1990) Tumor suppressor genes: the p53 and retinoblastoma sensitivity genes and gene products. *Biochim. Biophys. Acta* 1032, 119-136.

Lin, J. H., and Lu, A. Y. (2001) Interindividual variability in inhibition and induction of cytochrome P450 enzymes. Annu Rev Pharmacol Toxicol. 41, 535-567.

Lin, D., Fiscella, M., O'Connor, P. M., Jackman, J., Chen, M., Luo, L. L., Sala, A., Travali, S., Appella, E., Mercer, W. E. (1994). Constitutive expression of B-myb can bypass p53-induced Wafl/Cipl-mediated G1 arrest. *Proc. Natl. Acad. Sci. USA* 91, 10079-10083.

Liu, X., Constantinescu, S. N., Sun, Y., Bogan, J. S., Hirsch, D., Weinberg, R. A., and Lodish, H. F. (2000) Generation of mammalian cells stably expressing murine genes at predetermined levels. *Anal. Biochem.* 280, 20-28.

Liu, Y., Bohn, S. A., and Sherley, J. L. (1998a) Inosine-5'-monophosphate dehydrogenase is a rate-determining factor for p53-dependent growth regulation. *Mol. Biol. Cell* 9, 15-28.

Liu, Y., Riley, L. B., Bohn, S. A., Boice, J. A., Stadler, P. B., and Sherley, J. L. (1998b) Comparison of Bax, Wafl, and IMP dehydrogenase regulation in response to wild-type p53 expression under normal growth conditions. *J. Cellular Physiology* 177, 364-376.

Loeffler, M. and Potten, C. S. (1997). Stem cells and cellular pedigrees—a conceptual introduction. In *Stem Cells*, C. S. Potten, ed. (San Diego, Calif.: Harcourt Brace & Co.), pp. 1-28.

Matioli, G., Niewisch, H., and Vogel, H. (1970) Stochastic stem cell renewal. Rev. Europ. Etudes Clin. Et Biol. XV, 20-22.

Maurer, S. M., Firestone, R. B., and Scriver, C. R. (2000) Science's neglected legacy. *Nature* 405, 117-120.

Merok, J. L. and Sherley, J. L. (2001) Breaching the Kinetic Barrier to In Vitro Somatic Stem Cell Propagation. J. Biomed. Biotech 1, 24-26.

Mitaka, T., Sato, F., Mizuguchi, T., Yokono, T., Mochizuki, Y. (1999) Reconstruction of hepatic organoid by rat small hepatocytes and hepatic nonparenchymal cells. *Hepatology* 29, 111-125.

Moore, K. A., Ema, H., and Lemischka, I. R. (1997) In vitro maintenance of highly purified, transplantable hematopoetic stem cells. *Blood* 89, 4337-4347.

Murray, A. W. (1971) The biological significance of purine salvage. *Ann. Rev. Biochem.* 40, 811-826.

Nagai, M., Natsumeda, Y., and Weber, G. (1992) Proliferation-linked regulation of type II IMP dehydrogenase gene in human normal lymphocytes and HL-60 leukemic cells. *Cancer Res.* 52, 258-261.

Natsumeda, Y., Ohno, S., Kawasaki, H., Konno, Y., Weber, G., and Suzuki, K. (1990) Two distinct cDNAs for human IMP dehydrogenase. *J. Biol. Chem.* 265, 5292-5295.

McKay, R. (2000) Stem cells-hype and hope. Nature 406, 361-364.

Neutra, M. and Louvard, D. (1989) "Differentiation of intestinal cells in vitro", In *Epithelial Cells in Culture*, Alan R. Liss, pp. 363-398.

Nias, A. H. W. and Lajtha, L. G. (1965) "Clone size distribution in the study of inhomogeneity of growth rates in tissue culture" in Cell Culture, C. V. Ramakrishnan, ed. (Dr. W. Junk Publishers, Netherlands).

O'Connor, P. M., Jackman, J., Bae, I., Myers, T. G., Fan, S., Mutoh, M., Scudiero, D. A., Monks, A., Sausville, E. A., Weinstein, J. N., Friend, S., Fornace, Jr., A. J., and Kohn, K. W. (1997) Characterization of the p53 tumor suppressor pathway in cell lines of the National Cancer Institute anticancer drug screen and correlations with the growth-inhibitory potency of 123 anticancer agents. *Cancer Res.* 57, 4285-4300.

Petersen, B. E., Bowen, W. C., Patrene, K. D., Mars, W. M., Sullivan, A. K., Murase, N., Boggs, S. S., Greenberger, J. S., Goff, J. P. (1999) Bone marrow as a potential source of hepatic oval cells. *Science* 284, 1168-1170.

Phillips, R. L., Ernst, R. E., Brunk, B., Ivanova, N., Mahan, M. A., Deanehan, J. K., Moore, K. A., Overton, G. C., and Lemischka, I. R. (2000) The genetic program of hematopoetic stem cells. *Science* 288, 1635-1640.

Poldosky, D. K. (1993). Regulation of intestinal epithelial proliferation: a few answers, many questions. *Am. J. Physiol.* 264, G179-G186.

Potten, C. S. and Grant, H. K. (1998). The relationship between ionizing radiation-induced apoptosis and stem cells in the small and large intestine. *British J. of Cancer* 78, 993-1003.

Potten, C. S. and Morris, R. J. (1988) Epithelial stem cells in vivo. *J. Cell Sci. Suppl.* 10, 45-62.

Powers, M. J., Rodriguez, R. E., Griffith, L. G. (1997) Cell-substratum adhesion strength as a determinant of hepatocyte aggregate morphology. *Biotech. and Bioeng.* 53, 415-426.

Puck, T. T. and Marcus, P. I., J. (1956) Experimental Medicine 103, 653.

Quattrochi, L. C. and Guzelian, P. S. (2001) CYP3A regulation: from pharmacology to nuclear receptors. Drug Metab. Disposition 29, 615-622.

Quattrochi, L. C., Yockey, C. B., Barwick, J. L., and Guzelian, P. S. (1998) Characterization of DNA-binding proteins required for glucocorticoid induction of CYP3A23. Arch Biochem Biophys. 349, 251-260.

Redman, C. M., Avellino, M., Yu, S. (1983) "Secretion of Proalbumin by Canavanine-treated Hep-G2 Cells", J. Biol. Chem., 258, 3446-3452.

Rambhatla, L., Bohn, S. A., Stadler, P. B., Boyd, J. T., Coss, R. A., and Sherley, J. L. (2000). Cellular senescence: ex vivo p53-dependent asymmetric cell kinetics. *J. Biomed. Biotech*, 1, 27-36.

Rambhatla, L., Bohn, S. A., Stadler, P. B., Boyd, J. T., Coss, R. A., and Sherley, J. L. (2001). Cellular senescence: ex vivo p53-dependent asymmetric cell kinetics. *J. Biomed. Biotech* 1, 28-37.

Raucy, J. L. (2003) Regulation of CYP3A4 expression in human hepatocytes by pharmaceuticals and natural products. Drug Metab Dispos. 31, 533-539.

Raucy, J. L., Mueller, L., Duan, K., Allen, S. W., Strom, S., and Lasker, J. M. (2002) Expression and induction of CYP2C P450 enzymes in primary cultures of human hepatocytes. J Pharmacol Exp Ther. 302, 475-482.

Reisner, Y., Itzicovitch, L., Meshorere, A., and Sharon, N. (1978). Hematopoetic stem cell transplantation using mouse bone marrow and spleen cells fractionated by lectins. *Proc. Natl. Acad. Sci. USA* 75, 2933-2936.

Ross D. T., Scherf, U., Eisen, M. B., Perou, C. M., Rees, C., Spellman, P., Iyer, V., Jeffrey, S. S., Van de Rijn, M., Waltham, M., Pergamenschikov, A., Lee, J. C., Lashkari, D., Shalon, D., Myers, T. G., Weinstein, J. N., Botstein, D., and Brown, P. O. (2000) Systematic variation in gene expression patterns in human cancer cell lines. *Nat. Genet.* 24, 227-235.

Semino, C. E., Merok, J. R., Crane G. G., Panagiotakos, G., and Zhang, S. (2003) Functional differentiation of hepatocyte-like spheroid structures from putative liver progenitor cells in three-dimensional peptide scaffolds. *Differentiation* 71, 262-270.

Senda, M. and Natsumeda, Y. (1994) Tissue-differential expression of two distinct genes for human IMP dehydrogenase (E.C.1.1.1.205). *Life Sci.* 54, 1917-1926.

Sherley, J. L. (1991) Guanine nucleotide biosynthesis is regulated by the cellular p53 concentration. *J. Biol. Chem.* 266, 24815-24828.

Sherley, J. L. (2002) Asymmetric cell kinetics genes: The key to expansion of adult stem cells in culture. *Stem Cells* 20, 561-572.

Sherley, J. L. (1996) The p53 tumor suppressor gene as regulator of somatic stem cell renewal division. *Cope* 12, 9-10.

Sherley, J. L. (2000). Tumor Suppressor Genes and Cell Kinetics in the Etiology of Malignant Mesothelioma" in Sourcebook of Asbestos Diseases, G. A. Peters & B. J. Peters, eds. Peters and Peters (Santa Monica), Vol. 21, pp. 91-141.

Sherley, J. L., Stadler, P. B., and D. R. Johnson (1995a). Expression of the wildtype p53 antioncogene induces guanine nucleotide-dependent stem cell division kinetics. *Proc. Natl. Acad. Sci.* 92, 136-140.

Sherley, J. L., Stadler, P. B., and Stadler, J. S. (1995b) A quantitative method for the analysis of mammalian cell proliferation in culture in terms of dividing and non-dividing cells. *Cell Prolif.* 28, 137-144.

Sheu, H.-M., Chao, S.-C., Wong, T.-W., Lee, J. Y.-Y., and Tsai, J.-C. (1999) Human skin surface lipid film: an ultrastructural study and interaction with corneocytes and intercellular lipid lamellae of the statum corneum. *Brit. J. Derm.* 140, 385-391.

Smaglik, P. (2000) "Embryo stem-cell work gets NIH go-ahead", In *Nature* 406, p. 925.

Stadler, P. B., Pennacchi, J., and Sherley, J. L. (1994) Inosine-5'-monophosphate dehydrogenase activity is maintained in immortalized murine cells growth-arrested by serum deprivation. *Adv. Enzyme Regul.* 34, 91-106.

Takahashi, N., Takahashi, Y., Putnam, F. W. (1987) "Structural Changes and Metal Binding by Proalbumins and Other Amino—terminal Genetic Variants of Human serum Albumin", Proc. Natl. Acad. Sci. 84, 7403-7407.

Tiedeman, A. A. and Smith, J. M. (1991) Isolation and sequence of a cDNA encoding mouse IMP dehydrogenase. *Gene* 97, 289-293.

Tsien, R. (1998) The green fluorescent protein. *Annu. Rev. Riochem.* 67, 509-544.

Weissman, I. L. (2000) Stem cells: units of development, units of regeneration, and units of evolution. *Cell* 100, 157-168.

Willson, T. M. and Kliewer (2002) PXR, CAR and drug metabolism. Nature Rev. 1, 259-266.

Wilson, J. M. (1993). Vehicles for gene therapy. *Nature* 365, 691-692.

Yeuh, M.-F., Kawahara, M., Raucy, J. (2005) High volume bioassays to assess CYP3A4-mediated drug interactions: Induction and inhibition in a single cell line. Drug Metab. Disposition 33, 38-48.

Yuan, R., Mandani, S., Wei, X.-X., Reynolds, K., and Huang, S.-M. (2002) Evaluation of cytochrome P450 probe substrates commonly used by the pharmaceutical industry to study in vitro drug interactions. DMD 30, 1311-1319.

Zhang, J., Kuehl, P., Green, E. D., Touchman, J. W., Watkins, P. B., Daly, A., Hall, S. D., Maurel, P., Relling, M., Brimer, C., Yasuda, K., Wrighton, S. A., Hancock, M., Kim, R. B., Strom, S., Thummel, K., Russell, C. G., Hudson, J. R. Jr, Schuetz, E. G., and Boguski, M. S. (2001) The human pregnane X receptor: genomic structure and identification and functional characterization of natural allelic variants. Pharmacogenetics. 11, 555-552.

All references described herein are incorporated herein by reference.

We claim:

1. A method for deriving clonal cell lines of somatic liver stem cells comprising:
    a) plating at confluent cell density a starting liver cell population containing a population of somatic liver stem cells;
    b) culturing the starting liver cell population containing a population of somatic liver stem cells at confluent cell density of step a) in a culture media with reduced serum;
    c) adding to the culture media of step b) growth factors TGF-β and EGF, and a guanine nucleotide precursor having a xanthine nucleus, wherein said guanine nucleotide precursor having a xanthine nucleus is present in an amount of 50 μM-5 mM;
    d) culturing the starting liver cell population of step c) for a time sufficient to permit TGF-β and EGF to induce differentiation and growth arrest of non-stem cells and permit stem cell growth;
    e) expanding the cells of step d) in the culture media comprising 50 μM-5 mM of a guanine nucleotide precursor having a xanthine nucleus;
    f) growing individual cell colonies from the cells of step e) in the culture media comprising 50 μM-5 mM of a guanine nucleotide precursor having a xanthine nucleus, and transferring said individual colonies to single wells of a culture plate; and
    g) culturing and expanding said individual cell colonies that were isolated in step f) in the culture media comprising 50 μM-5 mM of a guanine nucleotide precursor having a xanthine nucleus resulting in expansion of said isolated cells thereby deriving clonal cell lines of somatic liver stem cells.

2. The method of claim 1, wherein the starting liver cell population of step a) to step d) is cultured in media that contains about 1% serum.

3. The method of claim 1, further comprising obtaining the starting liver cell population from a mammal.

4. The method of claim 1, wherein the starting liver cell population was previously isolated from a mammal.

5. The method of claim 1, wherein said guanine nucleotide precursor having a xanthine nucleus is present in an amount of 50 μM-1,500 μM.

6. The method of claim 1, wherein said guanine nucleotide precursor having a xanthine nucleus is xanthine, xanthosine or hypoxanthine.

7. A method of culturing and expanding somatic liver stem cells ex vivo, comprising:
    a) plating at confluent cell density a starting liver cell population isolated from a mammal containing a population of somatic liver stem cells;
    b) culturing the starting liver cell population containing a population of somatic liver stem cells at confluent cell density of step a) in a culture media with reduced serum;
    c) adding to the culture media of step b) growth factors TGF-β and EGF, and a guanine nucleotide precursor having a xanthine nucleus, wherein said guanine nucleotide precursor having a xanthine nucleus is present in an amount of 50 μM-5 mM;

d) culturing the starting liver cell population of step c) for a time sufficient to permit TGF-β and EGF to induce differentiation and growth arrest of non-stem cells and permit stem cell growth; and e) expanding the cells of step d) in the culture media comprising 50 μM-5 mM of a guanine nucleotide precursor having a xanthine nucleus.

8. The method of claim 7, wherein the starting liver cell population of step a) to step d) is cultured in media that contains about 1% serum.

9. The method of claim 1, wherein the starting liver cell population of step e) to step g) is cultured in media that contains about 10% serum.

10. The method of claim 1, wherein the starting liver cell population of step f) and step g) is cultured in media without growth factors TGF-β and EGF.

11. The method of claim 7, wherein the starting liver cell population of step e) is cultured in media that contains about 10% serum.

* * * * *